United States Patent
Vo-Dinh et al.

(10) Patent No.: US 9,662,389 B2
(45) Date of Patent: May 30, 2017

(54) FUNCTIONALIZED METAL-COATED ENERGY CONVERTING NANOPARTICLES, METHODS FOR PRODUCTION THEREOF AND METHODS FOR USE

(75) Inventors: Tuan Vo-Dinh, Chapel Hill, NC (US); Jon Scaffidi, Durham, NC (US); Molly Gregas, Durham, NC (US); Benoit Lauly, Durham, NC (US)

(73) Assignee: Duke University, Durham, NC (US)

( * ) Notice: Subject to any disclaimer, the term of this patent is extended or adjusted under 35 U.S.C. 154(b) by 785 days.

(21) Appl. No.: 12/843,188

(22) Filed: Jul. 26, 2010

(65) Prior Publication Data
US 2011/0129537 A1    Jun. 2, 2011

Related U.S. Application Data

(60) Provisional application No. 61/228,224, filed on Jul. 24, 2009.

(51) Int. Cl.
*A61K 9/16* (2006.01)
*A61K 41/00* (2006.01)
*A61K 47/48* (2006.01)

(52) U.S. Cl.
CPC .... *A61K 41/0066* (2013.01); *A61K 47/48315* (2013.01); *A61K 47/48861* (2013.01)

(58) Field of Classification Search
CPC .......... G01T 1/10; G01N 21/62; G01N 21/64; G21H 5/00; G03B 42/02; A61B 5/00; A61B 5/0059; A61B 5/0071; A61B 5/0093; A61B 5/05; A61B 5/0515; A61K 9/51; A61K 9/5115; A61K 49/00; A61K 49/001; A61K 49/0013; A61K 49/005
USPC ................ 424/465–489; 250/459.1
See application file for complete search history.

(56) References Cited

U.S. PATENT DOCUMENTS

| | | | |
|---|---|---|---|
| 5,023,139 A * | 6/1991 | Birnboim ........... | A61K 41/0042 428/402 |
| 2002/0034747 A1* | 3/2002 | Bruchez et al. ................. | 435/6 |
| 2002/0045045 A1* | 4/2002 | Adams .................... | B82Y 15/00 428/403 |
| 2002/0103517 A1* | 8/2002 | West .................... | A61K 41/0052 607/88 |
| 2004/0009349 A1* | 1/2004 | Brotzman et al. ........... | 428/379 |
| 2005/0130167 A1* | 6/2005 | Bao ...................... | A61K 49/0002 435/6.12 |
| 2006/0083694 A1 | 4/2006 | Kodas et al. | |
| 2006/0119853 A1 | 6/2006 | Baumberg et al. | |
| 2007/0212542 A1* | 9/2007 | Guo ....................... | B82Y 30/00 428/406 |
| 2008/0031883 A1 | 2/2008 | Torchilin et al. | |
| 2008/0248001 A1 | 10/2008 | Bourke | |
| 2009/0022783 A1 | 1/2009 | Lieberman et al. | |
| 2009/0294692 A1* | 12/2009 | Bourke et al. ............. | 250/459.1 |

OTHER PUBLICATIONS

International Search Report issued Dec. 2, 2010 in PCT/US 10/43243.

* cited by examiner

*Primary Examiner* — Micah-Paul Young
(74) *Attorney, Agent, or Firm* — Oblon, McClelland, Maier & Neustadt, L.L.P.

(57) ABSTRACT

A functionalized nanoparticle, having a core, optionally having a shell on at least a portion thereof, wherein the core contains a material that can convert applied X-ray energy into emitted UV energy and wherein the shell, when present, contains a plasmonics active material; wherein the nanoparticle has on a surface thereof at least one psoralen compound capable of activation by the emitted UV energy, and the use of the functionalized nanoparticle in a method of treating a cell proliferation disorder such as cancer.

74 Claims, 15 Drawing Sheets

Chemical structures of psoralen, 8-methoxypsoralen (8-MOP), 5-methoxypsoralen (5-MOP) and 4,5',8-trimethylpsoralen (TMP).

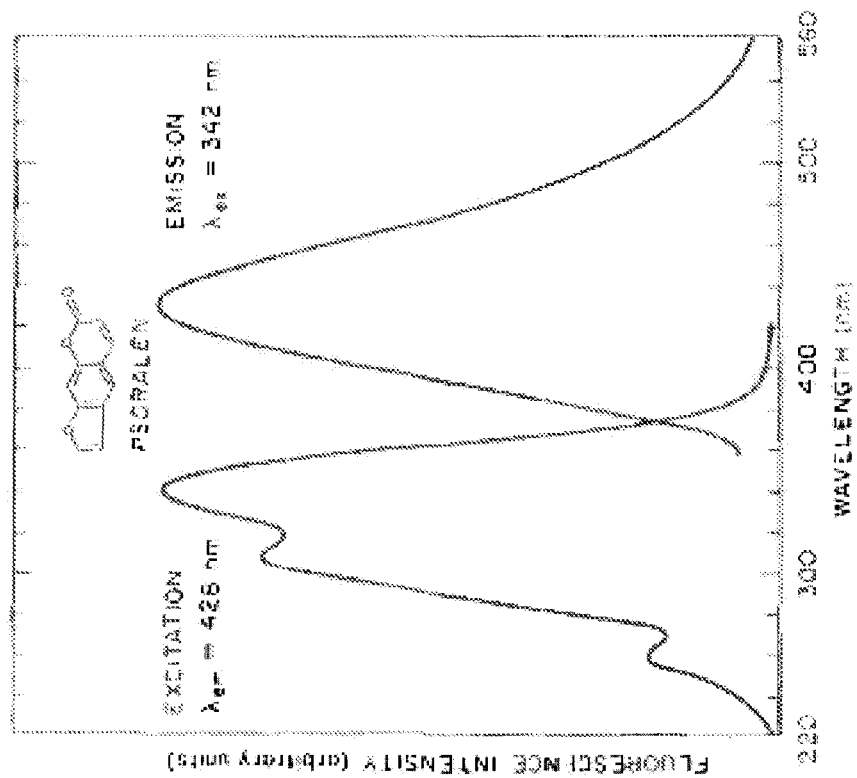
FIG. 2A Fluorescence emission and excitation spectra of psoralen in ethanol (10 μg/mL).

FUNCTIONALIZED METAL-COATED ENERGY CONVERTING NANOPARTICLES, METHODS FOR PRODUCTION THEREOF AND METHODS FOR USE

CROSS REFERENCE TO RELATED APPLICATIONS

This application claims priority to U.S. provisional patent application 61/228,224, filed Jul. 24, 2009, the entire contents of which are hereby incorporated by reference. This application is related to U.S. patent application Ser. No. 11/935,655, filed Nov. 5, 2007; U.S. patent application Ser. No. 12/059,484, filed Mar. 31, 2008; U.S. patent application Ser. No. 12/389,946, filed Feb. 20, 2009; U.S. patent application Ser. No. 12/417,779, filed Apr. 3, 2009; U.S. provisional patent application 61/171,152, filed Apr. 21, 2009; U.S. provisional patent application 61/161,328, filed Mar. 18, 2009; U.S. provisional patent application 61/171,158, filed Apr. 21, 2009; and U.S. provisional patent application 61/042,561, filed Apr. 4, 2008, the entire contents of each of which are hereby incorporated by reference.

The present invention was made under a joint research agreement between Immunolight, LLC and Duke University.

BACKGROUND OF THE INVENTION

Field of the Invention

The present invention relates to nanoparticles, having an optional plasmonics-active shell and functionalized with at least one photoactivatable pharmaceutical agent, that are capable of converting energy from one energy level to an energy level capable of activating the photoactivatable pharmaceutical agent, methods for the production of the nanoparticles and methods for their use, particularly in the treatment of cell proliferation disorders.

Description of the Related Art

More than a million individuals are diagnosed with cancer in the United States each year, and annual cancer diagnoses worldwide number above ten millon.[A] Although traditional approaches such as surgery, chemotherapy, radiation therapy, photodynamic therapy (PDT), and psoralen+UVA (PUVA) have shown some success in treating certain types of cancer, there is a strong need to develop effective, universally applicable, and non-invasive means of therapy. To that end, the rapidly developing field of nanomedicine has attempted to leverage the untapped potential of nanomaterials as a means of improving drug targeting to and uptake by tumors, locally activating therapeutic agents, and limiting side-effects which may negatively impact patients' quality of life.[B]

These attempts to use nanomaterials to cure cancer have typically taken one of three approaches. In the first approach, nanoparticles have been used to aid in transport and delivery of chemotherapeutic agents.[C] Such methodologies have shown some potential, particularly in reducing the unpleasant side-effects associated with chemotherapy.[D] In a second approach, the nanoparticles themselves have been used as a means of enhancing the normal effects of some more traditional treatment techniques.[E] Two promising techniques which fall into this category are induction of hyperthermia by illuminating gold nanoshells with infrared light,[F] or enhanced reactive oxygen species (ROS) generation using solid gold nanoshells and X-ray radiation.[G] The third use of nanomaterials for cancer therapy is combination of ROS-generating PDT drugs with nanomaterials which emit visible light when excited by X-ray radiation (scintillators).[H]

Of these three approaches, the third is perhaps the most intriguing and exhibits some unique advantages. In theory, only those cells which both take up the nanodrug and receive X-ray radiation stand a significant chance of dying during treatment. As a result, the side-effects associated with non-specific uptake of chemotherapeutic drugs should be greatly reduced. At the same time, radiation doses should theoretically be able to be reduced to a point where systemic effects are minor or nonexistent. Unfortunately, while such an approach with traditional PDT drugs may have potential in well-oxygenated tissue, reduced ROS generation in the inherently hypoxic environment of many tumors[I] is likely to limit the broader utility of ROS-dependent X-ray activatable therapies.

The field of nanobiotechnology has experienced an explosive growth due to improved understanding of the characteristics and properties of nanoparticles and to rapid advances in the methods for their fabrication. With ongoing improvements in the techniques and technology needed for consistent production of nanomaterials, as well as a continually-improving understanding of their characteristics and potential, there has been a steady increase in the variety of laboratory-fabricated nanoparticles. Even with these improvements in the research laboratory, however, the types of particles which are commercially available are still limited to just a few categories.

Two of the first types of nanoparticles reliably synthesized in the laboratory were solid metal nanospheres of gold and silver,[1] typically produced in aqueous solution using a metal salt and a suitable reductant such as sodium citrate or sodium borohydride. Improvements in wet synthetic techniques since these early studies have expanded the range of solid noble metal nanoparticle shapes to include silver rods,[2-5] plates,[6-10] prisms[11] and cubes,[12,13] as well as gold rods,[14-24] disks,[25-27] plates,[28-30] prisms,[31-33] cubes[34,35] and stars.[36-38] Each of these size-tunable particle shapes and morphologies exhibit unique plasmonic properties which can strongly enhance electromagnetic fields, making them useful for both intracellular and extracellular biochemical sensing of biotargets such as DNA and mRNA,[39-48] or proteins and peptides[49,50] via surface plasmon resonance[39,51-54] or surface-enhanced Raman scattering (SERS).[40-48,55] An added advantage of noble metal nanoparticles (e.g., gold and silver) is that they are easily functionalized and essentially non-toxic to cells and higher organisms, making in vivo and in vitro bioanalyses practical.

Somewhat more recently, dye-doped[56-63] and dye-bound[64] silicon dioxide ($SiO_2$) nanoparticles have also found significant use as substrates for biochemical sensing when functionalized with nucleic acids, peptides or proteins.[65 and refs therein] Like gold and silver, $SiO_2$ is particularly appealing for in vivo and in vitro sensing because it is easily fabricated, easily functionalized and relatively non-toxic.

Intrinsically fluorescent semiconductor quantum dots (e.g. Cd:Te, Cd:Se, Zn:S, etc.) have been used for a range of applications including analytical chemistry, biochemical sensing, and study of cellular uptake, fate and transport.[66-69] The inherent toxicity of cadmium limits the utility of these materials in vivo, but they are eminently suited to a wide range of short-term in vitro studies during which longer-term toxicity is not an issue.

One approach to minimize the toxicity discussed above is to coat intrinsically-toxic nanomaterials with $SiO_2$,[70-75] thereby limiting the bioavailability of whatever toxins are present. This approach, in fact, has the potential to passivate a wide range of nanomaterials or, alternatively, allow more facile surface functionalization with biochemically-sensitive species. To this end, a number of researchers have added $SiO_2$ shells to quantum dots,[70-75] iron oxide,[76-78] or solid noble metal nanoparticles.[79-84] Alternatively, $SiO_2$ nanoparticles themselves can be coated with gold or silver to produce plasmonic nanoshells which can be tuned from the near UV to the near IR.[85-95] Various photochemical methods have been reported for the fabrication of gold nanoparticles and gold films [A. Pal, T. Pal, D. L. Stokes, and T. Vo-Dinh, *"Photochemically prepared gold nanoparticles: A substrate for surface-enhanced Raman scattering"*, Current Science, 84, 1342-1346 (2003); M. Volcan, D. L. Stokes and T. Vo-Dinh *"A Sol-Gel Derived AgCl Photochromic Coating on Glass for SERS Chemical Sensor Application"*, Sensors and Actuators B, 106, 660-667 (2005)] A. Pal, D. L. Stokes and T. Vo-Dinh, *"Photochemically Prepared Gold Metal film in a Carbohydrate-based Polymer: a Practical Solid substrate for Surface-enhanced Raman Scattering, Current Science*, 87, 486-491 (2004) and references therein].

There are also wet chemistry methods described in the literature [Oldenburg, S. J., Averitt, R. D., Westcott, S. L., and Halas, N. J. *Nanoengineering of Optical Resonances. Chemical Physics Letters* 288, 243-247 (1998); Jensen, R. A, Sherin, J. and Emory, S. R. *Single Nanoparticle Based Optical pH Probe. Applied spectroscopy*, 61, 8, 832-838 (2007); Oldenburg S. J., Westcott S. L., Averitt R. D., and Halas, N. J. *Surface enhanced Raman scattering in the near infrared using metal nanoshell substrates. Journal of Chemical Physics*, 111, 10, 4729-4735 (1999); and refrences therein]. An approach to form a gold shell around a core material is seed-mediated growth. The first step involves the use of chemical linkers to attach small Au or Ag seeds (from few nanometers to larger seeds depending on the core dimension) on the core surface. Several linkers can be used; a direct approach commonly described in the literature is to aminate the surface of the material to allow the adsorption of the seeds. Molecules with dual functionality act as linkers; an amino group to adsorb to the seeds or a thiol group to covalently bond the seeds on one side, and a carboxy-group, phosphonate-group, sulfonate-group on the other side to bind to the core surface, such as $Y_2O_3$, silica, polystyrene. Other approaches include using different coupling chemistry to bind two chemical groups attach to the core surface and the seeds. EDC (1-Ethyl-3-[3-dimethylaminopropyl]carbodiimide hydrochloride) -mediated coupling chemistry, for instance, enables the crosslinking of an amine and a carboxyl group. N-hydroxysuccinimide (NHS) coupling chemistry enables the formation of an amide bond between a primary amine and the succinimide ester. The second step in the seed mediated growth involves the attachment of additional gold, silver, silica, titania, alumina, yttria, etc. onto the nucleated seeds. As an example, a common approach to ripening of a gold layer is to use potassium carbonate and $HAuCl_4$ in the presence of formaldehyde. Alkoxides are frequently employed for thickening of silica or titania shells, and similar precursor compounds can be used when forming shells of alumina, yttria, etc.

Phototherapy There are two main types of reactions in phototherapy:

Type I reactions involve electrons and hydrogen atoms, which are transferred between photo-active molecules (also called photosensitizers) and substrates or solvent molecules. Oxygen may participate in subsequent reactions: e.g., psoralens in photopheresis and PUVA.

Type II reactions involve singlet oxygen formation by energy transfer from PA molecules in the lowest triplet state to oxygen in the ground state: e.g., photodynamic therapy (PDT).

Psoralen System. Psoralen (FIG. 1) is the parent compound in a family of natural products known as furocoumarins. Psoralens are a class of photo-mutagenic and photo-chemotherapeutic molecules that covalently modify nucleic acids. They belong the family of small molecules that intercalate into and photoalkylate double stranded DNA. The primary target of psoralens are thymidine residues, and these molecules form both monoadducts and interstrand crosslinks The reaction takes place between the 3,4 (pyrone) or 4',5' (furan) double bonds of the psoralen and the 5,6 double bond in pyrimidines.

Psoralen compounds absorb UVA and UVB photons, and emit visible light. FIGS. 2A and 2B show excitation and emission fluorescence spectra of psoralens. [Source: T. Vo-Dinh et al, J. Agric. Food Chem., 36, 335 (1988)]

U.S. Pat. No. 6,235,508 further teaches that psoralens are naturally occurring compounds which have been used therapeutically for millennia in Asia and Africa. The action of psoralens and light has been used to treat vitiligo and psoriasis (PUVA therapy; Psoralen Ultra Violet A). Psoralen is capable of binding to nucleic acid double helices by intercalation between base pairs; adenine, guanine, cytosine and thymine (DNA) or uracil (RNA). Upon sequential absorption of two UV-A photons, psoralen in its excited state reacts with a thymine or uracil double bond and covalently attaches to both strands of a nucleic acid helix. The crosslinking reaction appears to be specific for a thymine (DNA) or a uracil (RNA) base. Binding proceeds only if psoralen is intercalated in a site containing thymine or uracil, but an initial photoadduct must absorb a second UVA photon to react with a second thymine or uracil on the opposing strand of the double helix in order to crosslink each of the two strands of the double helix, as shown below. This is a sequential absorption of two single photons as shown, as opposed to simultaneous absorption of two or more photons.

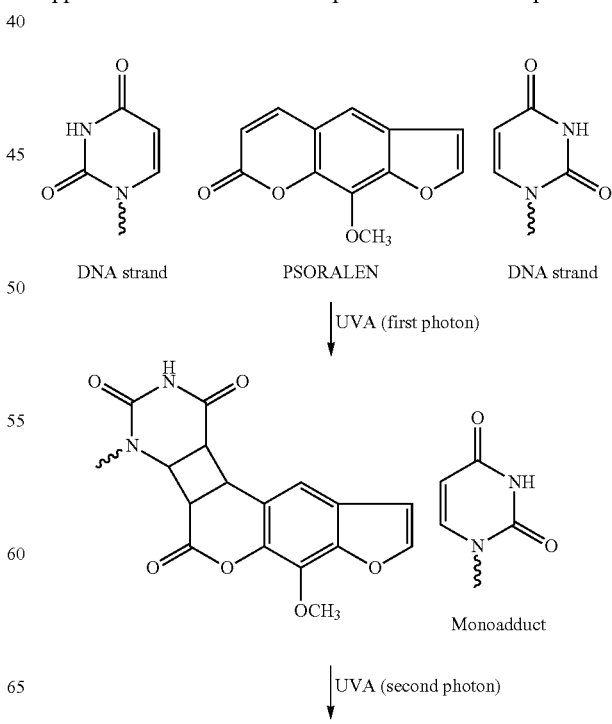

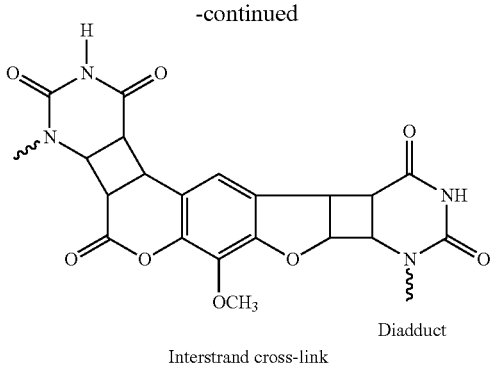

Interstrand cross-link

Diadduct

In addition, the reference teaches that 8-MOP is unsuitable for use as an antiviral, because it damages both cells and viruses. Lethal damage to a cell or virus occurs when the psoralen is intercalated into a nucleic acid duplex in sites containing two thymines (or uracils) on opposing strands but only when it sequentially absorbs 2 UVA photons and thymines (or uracils) are present. U.S. Pat. No. 4,748,120 of Wiesehan is an example of the use of certain substituted psoralens by a photochemical decontamination process for the treatment of blood or blood products.

Additives, such as antioxidants are sometimes used with psoralens, such as 8-MOP, AMT and I-IMT, to scavenge singlet oxygen and other highly reactive oxygen species formed during photoactivation of the psoralens. It is well known that UV activation creates such reactive oxygen species, which are capable of seriously damaging otherwise healthy cells. Much of the viral deactivation may be the result of these reactive oxygen species rather than any effect of photoactivation of psoralens. Regardless, it is believed that no auto vaccine effect has been observed.

Research in this field over-simplifies mechanisms involved in the photoactivating mechanism and formation of highly reactive oxygen species, such as singlet oxygen. Both may lead to inactivating damage of tumor cells, viruses and healthy cells. However, neither, alone or combined, lead to an auto vaccine effect. This requires an activation of the body's own immune system to identify a malignant cell or virus as threat and to create an immune response capable of lasting cytotoxic effects directed to that threat. It is believed, without being limiting in any way, that photoactivation and the resulting apoptosis of malignant cells that occurs in extracorporeal photopheresis causes the activation of an immune response with cytotoxic effects on untreated malignant cells. While the complexity of the immune response and cytotoxic effects is fully appreciated by researchers, a therapy that harnesses the system to successfully stimulate an auto vaccine effect against a targeted, malignant cell has been elusive, except for extracorporeal photopheresis for treating lymphoma.

Midden (W. R. Midden, Psoralen DNA photobiology, Vol II (ed. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes.

U.S. Pat. No. 6,235,508 teaches that 8-MOP and AMT are unacceptable photosensitizers, because each indiscriminately damages both cells and viruses. Studies of the effects of cationic side chains on furocoumarins as photosensitizers are reviewed in Psoralen DNA Photobiology, Vol. I, ed. F. Gaspano, CRC Press, Inc., Boca Raton, Fla., Chapter 2. U.S. Pat. No. 6,235,508 gleans the following from this review: most of the amino compounds had a much lower ability to both bind and form crosslinks to DNA compared to 8-MOP, suggesting that the primary amino functionality is the preferred ionic species for both photobinding and crosslinking.

U.S. Pat. No. 5,216,176 of Heindel discloses a large number of psoralens and coumarins that have some effectiveness as photoactivated inhibitors of epidermal growth factor. Halogens and amines are included among the vast functionalities that could be included in the psoralen/coumarin backbone. This reference is incorporated herein by reference.

U.S. Pat. No. 5,984,887 discloses using extracorporeal photopheresis with 8-MOP to treat blood infected with CMV. The treated cells as well as killed and/or attenuated virus, peptides, native subunits of the virus itself (which are released upon cell break-up and/or shed into the blood) and/or pathogenic noninfectious viruses are then used to generate an immune response against the virus, which was not present prior to the treatment.

A survey of known treatment methods reveals that these methods tend to face a primary difficulty of differentiating between normal cells and target cells when delivering treatment, often due to the production of singlet oxygen which is known to be non-selective in its attack of cells, as well as the need to perform the processes ex vivo, or through highly invasive procedures, such as surgical procedures in order to reach tissues more than a few centimeters deep within the subject.

U.S. Pat. No. 5,829,448 describes sequential and simultaneous two photon excitation of photo-agents using irradiation with low energy photons such as infrared or near infrared light (NRI). A single photon and simultaneous two photon excitation is compared for psoralen derivatives, wherein cells are treated with the photo agent and are irradiated with NRI or UV radiation. The patent suggests that treating with a low energy irradiation is advantageous because it is absorbed and scattered to a lesser extent than UV radiation. However, the use of NRI or UV radiation is known to penetrate tissue to only a depth of a few centimeters. Thus any treatment deep within the subject would necessarily require the use of ex vivo methods or highly invasive techniques to allow the irradiation source to reach the tissue of interest. Also, this patent does not describe initiation energy sources emitting energy other than UV, visible, and near infrared energy; energy upgrading other than within the range corresponding to UV and IR light, and downgrading from high to low energy.

Chen et al., J. Nanosci. and Nanotech., 6:1159-1166 (2006); Kim et al., JACS, 129:2669-2675 (2007); U.S. 2002/0127224; and U.S. Pat. No. 4,979,935 each describe methods for treatment using various types of energy activation of agents within a subject. However, each suffers from the drawback that the treatment is dependent on the production of singlet oxygen to produce the desired effect on the tissue being treated, and is thus largely indiscriminate in affecting both healthy cells and the diseased tissue desired to be treated.

U.S. Pat. No. 6,908,591 discloses methods for sterilizing tissue with irradiation to reduce the level of one or more active biological contaminants or pathogens, such as viruses, bacteria, yeasts, molds, fungi, spores, prions or similar agents responsible, alone or in combination, for transmissible spongiform encephalopathies and/or single or multicellular parasites, such that the tissue may subsequently be used in transplantation to replace diseased and/or otherwise defective tissue in an animal. The method may include the use of a sensitizer such as psoralen, a psoralen-derivative or other photosensitizer in order to improve the effectiveness of the irradiation or to reduce the exposure necessary to sterilize the tissue. However, the method is not suitable for treating a patient and does not teach any mechanisms for stimulating the photo sensitizers, indirectly.

U.S. Pat. No. 5,957,960 discloses a two-photon excitation device for administering a photodynamic therapy to a treatment site within a patient's body using light having an infrared or near infrared waveband. However, the reference fails to disclose any mechanism of photoactivation using energy modulation agent that converts the initiation energy to an energy that activates the activatable pharmaceutical agent and also use of other energy wavebands, e.g., X-rays, gamma-rays, electron beam, microwaves or radio waves.

U.S. Pat. No. 6,235,508 discloses antiviral applications for psoralens and other photoactivatable molecules. It teaches a method for inactivating viral and bacterial contaminants from a biological solution. The method includes mixing blood with a photosensitizer and a blocking agent and irradiating the mixture to stimulate the photo sensitizer, inactivating substantially all of the contaminants in the blood, without destroying the red blood cells. The blocking agent prevents or reduces deleterious side reactions of the photosensitizer, which would occur if not in the presence of the blocking agent. The mode of action of the blocking agent is not predominantly in the quenching of any reactive oxygen species, according to the reference.

Also, U.S. Pat. No. 6,235,508 suggests that halogenated photosensitizers and blocking agents might be suitable for replacing 8-methoxypsoralen (8-MOP) in photopheresis and in treatment of certain proliferative cancers, especially solid localized tumors accessible via a fiber optic light device or superficial skin cancers. However, the reference fails to address any specific molecules for use in treating lymphomas or any other cancer. Instead, the reference suggests a process of photopheresis for antiviral treatments of raw blood and plasma.

U.S. Pat. No. 6,235,508 teaches away from 8-MOP and 4'-aminomethyl-4,5',8-trimethylpsoralen (AMT) and many other photoactivatable molecules, which are taught to have certain disadvantages. Fluorescing photosensitizers are said to be preferred, but the reference does not teach how to select a system of fluorescent stimulation or photoactivation using fluorescent photosensitizers. Instead, the fluorescing photosensitizer is limited to the intercalator that is binding to the DNA. The reference suggests that fluorescence indicates that such an intercalator is less likely to stimulate oxygen radicals.

U.S. published application 2002/0127224 discloses a method for a photodynamic therapy comprising administering light-emitting nanoparticles and a photoactivatable agent, which may be activated by the light re-emitted from the nanoparticles via a two-photon activation event. An initiation energy source is usually a light emitting diode, laser, incandescent lamp, or halogen light, which emits light having a wavelength ranging from 350 to 1100 nm. The initiation energy is absorbed by the nanoparticles. The nanopartuicles, in turn, re-emit light having a wavelength from 500 to 1100 nm, preferably, UV-A light, wherein the re-emitted energy activates the photoactivatable agent. Kim et al., (JACS, 129:2669-75, Feb. 9, 2007) discloses indirect excitation of a photosensitizing unit (energy acceptor) through fluorescence resonance energy transfer (FRET) from the two-photon absorbing dye unit (energy donor) within an energy range corresponding to 300-850 nm. These references do not describe initiation energy sources emitting energy other than UV, visible, and near infrared energy; energy upgrading other than within the range corresponding to wavelength of 350-1100 nm, and downgrading from high to low energy.

These references fail to disclose any mechanism of photoactivation of photoactivatable molecules other than by direct photoactivation by UV, visible, and near infrared energy.

Therefore, there still exists a need for better and more effective treatments that can more precisely target the diseased cells without causing substantial side-effects or collateral damages to healthy tissues, and which are capable of treating disorders by non-invasive or minimally invasive techniques.

Cell Penetrating Peptides (CPP) and Nuclear Targeting Peptides (NTP) for Cellular Delivery of Nanoparticles An important element involves effective intracellular delivery of the nanoparticle-based drug systems into the cells and inside the nucleus in order to bind to DNA. Viral vectors have been proposed for DNA delivery but these approaches are limited by non-specificity and inherent risks of virus-induced complications. Liposomes and micelles have been used for the delivery of water soluble drugs and poorly soluble drugs, respectively. Coated with polyethylene glycol, PEG (i.e. PEGylated), liposomes have been extensively investigated because of their capability to remain sufficiently long in the blood in order to accumulate in various pathological areas(passive targeting) with the compromised leaky vasculature, such as tumors [D. D. Lasic, F. J. Martin (Eds.), Stealth Liposomes, CRC Press, Boca Raton, 1995.].

It was demonstrated in 1988 that the 86-mer trans-activating transcriptional activator, Tat, protein encoded by HIV-1, was efficiently internalized by cells in vitro when introduced in the surrounding media [M Green, P. M. Loewenstein, *Autonomous functional domains of chemically synthesized human immunodeficiency virus tat trans-activator protein*, Cell 55 (1988) 1179-1188; A. D. Frankel, C. O. Pabo, Cellular uptake of the tat protein from human immunodeficiency virus, Cell 55 (1988) 1189-1193.]. It has been shown that short peptides could provide an active transport mechanism to facilitate nanoparticles to cross cell membranes and enter cells and nucleus [R. D. Egleton, T. P. Davis, *Bioavailability and transport of peptides and peptide drugs into the brain*, Peptides 18 (1997) 1431-1439.]. In this approach, which has become a useful and effective technique for overcoming the cellular barrier for intracellular drug delivery, certain proteins or peptides can be tethered to drug to form a construct that exhibits the capability to translocate across the plasma membrane and deliver the payload intracellularly. These proteins or peptides contain domains of less than 20 amino acids,are often referred to as Protein Transduction Domains (PTDs), or cell-penetrating peptides (CPPs). Nuclear Targeting Peptides (NTPs) are CPPs that allow intracellular transport of drug systems inside the nucleus.

A wide variety of peptides, either derived from proteins or synthesized chemically, have been developed and used for cellular membrane translocation. These peptides include Antennapedia (Antp) [A. Joliot, C. Pernelle, H. Deagostini-Bazin, A. Prochiantz, *Antennapedia homeobox peptide regulates neural morphogenesis*, Proc. Natl. Acad. Sci. USA 88 (1991) 1864-1868], VP22 [G. Elliott, P. O'Hare, *Intercellular trafficking and protein delivery by a herpesvirus structural protein*, Cell 88 (1997) 223-233], transportan [M. Pooga, M. Hallbrink, M. Zorko, U. Langel, *Cell penetration* by transportan, *FASEB J.* 12 (1998) 67-77.], model amphipathic peptide MAP [J. Oehlke, et al., *Cellular uptake of an alpha-helical amphipathic model peptide with the potential to deliver polar compounds into the cell interior non-endocytically, Biochim. Biophys. Acta* 1414 (1998) 127-139.], signal sequence-based peptides [M. Rojas, J. P. Donahue, Z. Tan, Y. Z. Lin, *Genetic engineering of proteins with cell membrane permeability, Nat. Biotechnol.* 16 (1998) 370-375.1 and synthetic polyarginines [S. Futaki, et al., *Arginine-rich peptides. An abundant source of membrane-permeable peptides having potential as carriers for intracellular protein delivery, J. Biol. Chem.* 276 (2001) 5836-5840.]

TAT peptide (TATp), which is derived from the transcriptional activator protein encoded by human immunodeficiency virus type 1 (HIV-1) [K. T. Jeang, H. Xiao, E. A. Rich, *Multifaceted activities of the HIV-1transactivator of transcription, Tat, J. Biol. Chem.* 274 (1999) 28837-288401] has been a widely used CPP system. The transduction ability of Tat protein is due to the positive charge in the transduction domain of TAT (TATp), which extends from residues 47-57: Tyr-Gly-Arg-Lys-Lys-Arg-Arg-Gln-Arg-Arg-Arg, which contains six arginines (Arg) and two lysine residues [S. R. Schwarze, K. A. Hruska, S. F. Dowdy, Protein transduction: unrestricted delivery into all cells? Trends Cell Biol. 10 (2000) 290-295.]

Josephson et al provided the first example of CPP-mediated nanoparticulate delivery in 1999 [L. Josephson, C. H. Tung, A. Moore, R. Weissleder, High-efficiency intracellular magnetic labeling with novel superparamagnetic-Tat peptide conjugates, Bioconjug. Chem. 10 (1999) 186-191. The fluorescence microscopy studies on the live cells revealed that The conjugate was shown to accumulate first in lysosomes, followed by intense localization within the nuclei.

Other CPP systems have also been used for cellular uptake and drug delivery. MAP has the fastest uptake, followed by transportan, TATp (48-60), and penetratin. Similarly, MAP has the highest cargo delivery efficiency, followed by transportan, TATp (48-60), and penetratin. For a review, see Ref [Vladimir P. Torchilin, *Tat peptide-mediated intracellular delivery of pharmaceutical nanocarriers, Advanced Drug Delivery Reviews* 60 (2008) 548-558, and reference therein]

SUMMARY OF THE INVENTION

Accordingly, one object of the present invention is to provide a functionalized nanoparticle that can convert X-ray energy into UV energy, and thereby activate a psoralen molecule bound directly or indirectly to the nanoparticle core.

A further object of the present invention is to provide a method for treatment of a cell proliferation disorder, such as cancer, by administration of a functionalized nanoparticle of the present invention to a subject in need thereof, and applying X-ray energy to the functionalized nanoparticle in situ in the subject.

Another object of the present invention is to provide a pharmaceutical composition comprising the functionalized nanoparticle of the present invention.

These and other objects of the present invention, either individually or in combinations thereof, have been satisfied by the discovery of a functionalized nanoparticle, comprising:
 a core, optionally having a shell on at least a portion thereof, wherein the core comprises a material that can convert applied X-ray energy into emitted UV energy and wherein the shell, when present, comprises a plasmonics active material;
 wherein the nanoparticle has on a surface thereof at least one psoralen compound capable of activation by the emitted UV energy.

BRIEF DESCRIPTION OF THE FIGURES

The above and other objects, features and advantages of the present invention will become more apparent from the following detailed description taken with the accompanying drawings in which:

FIGS. 2A and 2B show excitation and emission fluorescence spectra of psoralens.

DETAILED DESCRIPTION OF THE PREFERRED EMBODIMENTS

Figure 1:
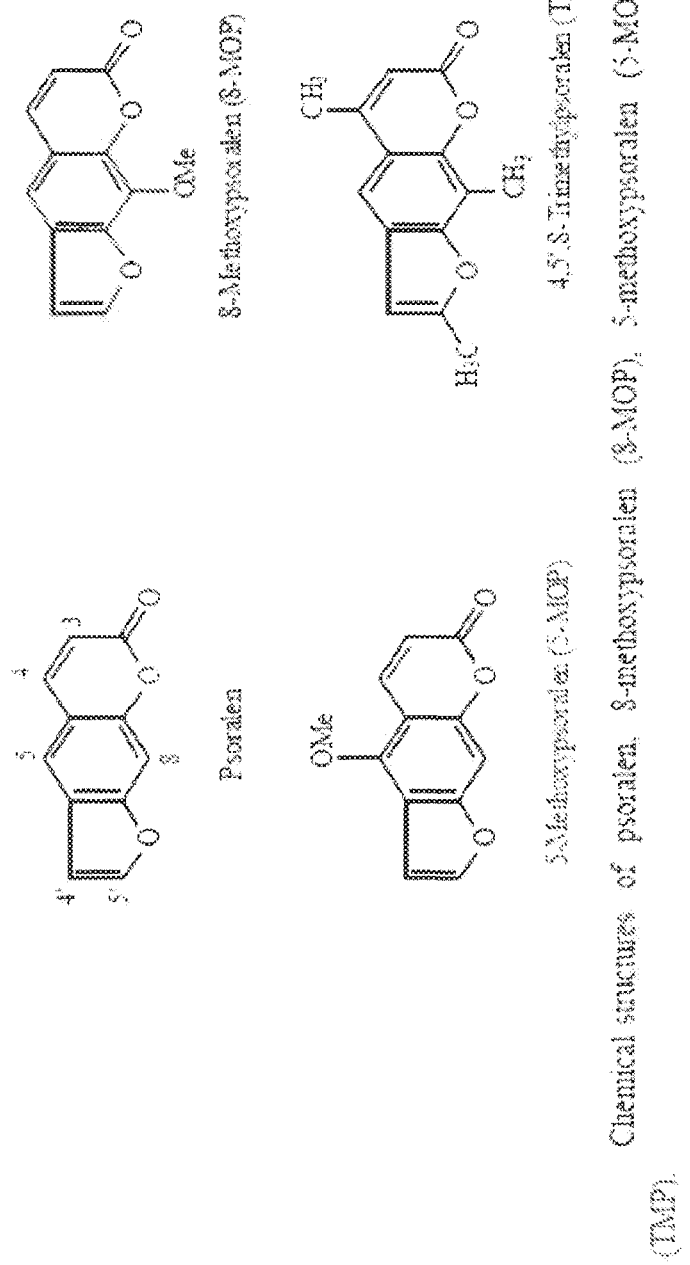
FIG. 1 shows the chemical structures of various psoralen compounds.
Figure 2B:
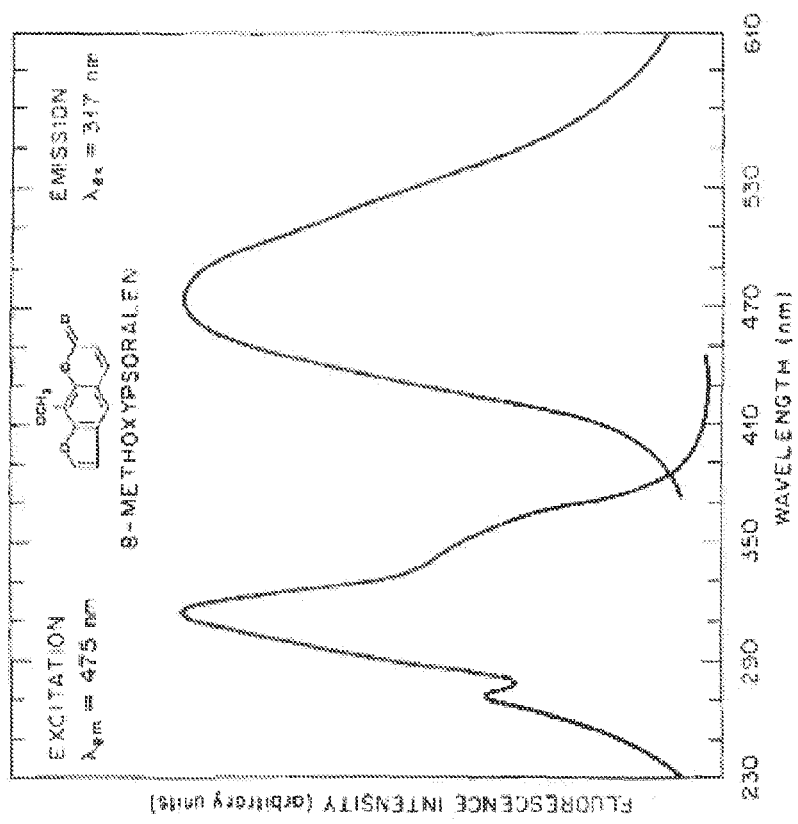

One embodiment of the present invention relates to a functionalized nanoparticle, comprising:
 a core, optionally having a shell on at least a portion thereof, wherein the core comprises an energy modulation agent that can convert applied X-ray energy into an emitted UV energy, and wherein the shell, when present, comprises either (i) a plasmonics-active material, (ii) a material designed to protect the core, (iii) a biocompatible material designed to make the core biocompatible, or a combination thereof;

wherein the nanoparticle has on a surface thereof at least one psoralen or psoralen derivative capable of activation by the emitted UV energy.

A further embodiment of the present invention relates to a method for using the functionalized nanoparticle of the present invention in a method for treating a cell proliferation disorder, particularly the treatment of cancer, wherein the method comprises administering to a subject in need thereof the functionalized nanoparticle of the present invention, and applying X-ray energy, which is converted by the nanoparticle core to a UV energy that is emitted from the core, wherein the emitted UV energy activates the psoralen or psoralen derivative, which upon activation causes a desired cellular change, thus treating the cell proliferation disorder. In a preferred embodiment, the core has on its surface a plasmonics active material, preferably a shell of gold or silver or other materials, which enhances or intensifies either or both of the applied X-ray energy or emitted UV energy.

Various methods and materials for the treatment of cell proliferation disorders and for photobiomodulation are disclosed in U.S. patent application Ser. No. 11/935,655, filed Nov. 5, 2007; U.S. patent application Ser. No. 12/059,484, filed Mar. 31, 2008; U.S. patent application Ser. No. 12/389, 946, filed Feb. 20, 2009; U.S. patent application Ser. No. 12/417,779, filed Apr. 3, 2009; U.S. provisional patent application 61/171,152, filed Apr. 21, 2009; U.S. provisional patent application 61/161,328, filed Mar. 18, 2009; U.S. provisional patent application 61/171,158, filed Apr. 21, 2009; and U.S. provisional patent application 61/042,561, filed Apr. 4, 2008, all of which have been incorporated by reference above. The present invention represents an improvement and refinement of the methods and materials of these previous applications, particularly for the area of treatment of cell proliferation disorders, preferably cancer treatment.

1) The energy modulation agent materials for the core of the present invention functionalized nanoparticle can include any materials that can absorb X ray and emit UV energy in order to activate the psoralen or psoralen derivative. The energy modulation agent materials include, but are not limited to metals (gold, silver, copper, gallium, platinum, palladium, nickel, aluminum, etc.) and metal alloys comprising a combination of the above materials metal alloys metal oxides (e.g., $TiO_2$)

quantum dots;

semiconductor materials;

scintillation and phosphor materials;

materials that exhibit X-ray excited luminescence (XEOL);

organic solids, metal complexes, inorganic solids, crystals, rare earth materials (lanthanides), polymers, scintillators, phosphor materials, etc.; and materials that exhibit excitonic properties.

Quantum dots, semiconductor nanostructures. Various materials related to quantum dots, semiconductor materials, etc. can be used as energy modulation agent systems. For example CdS-related nanostructures have been shown to exhibit X-ray excited luminescence in the UV-visible region [Hua et al, *Rev. Sci. Instrum.*, 73, 1379, 2002].

Scintillator Materials as energy modulation agent systems. Various scintillator materials can be used as energy modulation agents since they absorb X-ray and emit luminescence emission, which can be used to excite the psoralen or psoralen derivative. For example, single crystals of molybdates can be excited by X-ray and emit luminescence around 400 nm [Mirkhin et al, *Nuclear Instrum. Meth. In Physics Res. A*, 486, 295 (2002].

Solid Materials as energy modulation agent systems: Various solid materials can be used as energy modulation agents due to their X-ray excited luminescence properties. For example CdS (or CsCl) exhibit luminescence when excited by soft X-ray [Jaegle et al, *J. Appl. Phys.*, 81, 2406, 1997].

XEOL materials: lanthanides or rare earth materials, such as $Y_2O_3$ [L. Soderholm, G. K Liu, Mark R. Antonioc, F. W Lytle, *X-ray excited optical luminescence .XEOL. detection of x-ray absorption fine structure .XAFZ, J. Chem. Phys,*109, 6745, 1998], Masashi Ishiia, Yoshihito Tanaka and Tetsuya Ishikawa, Shuji Komuro and Takitaro Morikawa, Yoshinobu Aoyagi, *Site-selective x-ray absorption fine structure analysis of an optically active center in Er-doped semiconductor thin film using x-ray-excited optical luminescence, Appl. Phys. Lett,* 78, 183, 2001]

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as $Er^{3+}$ doped $BaTiO_3$ nanoparticles and $Yb^{3+}$ doped $CsMnCl_3$) are suitable in various embodiments of the invention.

Core-shell particle characterization: A number of material characterization techniques have the potential to provide useful information regarding the size and structure of the core-shell particles produced in this work. UV-visible absorption spectroscopy, for example, can quickly and easily provide information regarding whether plasmonic gold structures in solution are solid gold nanoparticles or shells deposited around a dielectric core.[86-93] X-ray diffraction spectroscopy (XRD) provides similar information, with the added benefit that core and shell identity and structure (cubic vs. hexagonal or amorphous structures, for example) can often be definitively determined.[130-132] Transmission electron microscopy (TEM) provides further analytical information by allowing direct visualization with nanometer-scale resolution.

Figure 3:
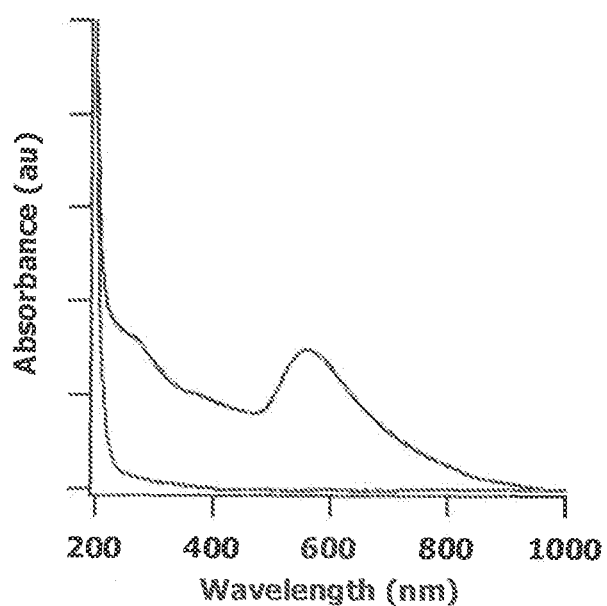
FIG. 3 shows UV-visible absorption spectra of cubic $Y_2O_3$ and gold-coated $Y_2O_3$ dispersed using 10 m$\underline{M}$ tri-arginine.

FIG. 3 shows UV-visible absorption spectra of cubic $Y_2O_3$ and gold-coated $Y_2O_3$ dispersed using 10 m$\underline{M}$ tri-arginine. The absorption spectrum of $Y_2O_3$ alone (lower trace) is fairly featureless, showing absorption due to the tri-arginine near 200 nm and a gentle slope associated with scattering and absorption by the $Y_2O_3$ nanoparticles extending into the visible portion of the spectrum. The gold-coated $Y_2O_3$ (upper trace), on the other hand, exhibit a strong absorption band at 546 nm which is characterisitic of the plasmonics resonance band due to the gold shell around the $Y_2O_3$ cores. Prior experience and the scientific literature indicate that this plasmon band would be centered at or below 530 nm if it were due to solid gold nanoparticles in solution.[133-139] Red-shifting of the plasmon absorption to 546 nm is consistent with the presence of a gold shell around a dielectric core. Since there are no other potential core materials in our initial reaction solutions, this core material can be assigned to $Y_2O_3$. Previously published models for plasmonic absorption by gold shells around $SiO_2$ nanoparticles[86-93] suggest that the shell thickness for these gold-coated $Y_2O_3$ nanoparticles is similar to the radius of the dielectric core. Any further calculation of the core-shell radial ratio based purely on UV-visible absorption spectra is hindered by the irregular shape and polydispersity of the $Y_2O_3$ cores.

Figure 4:
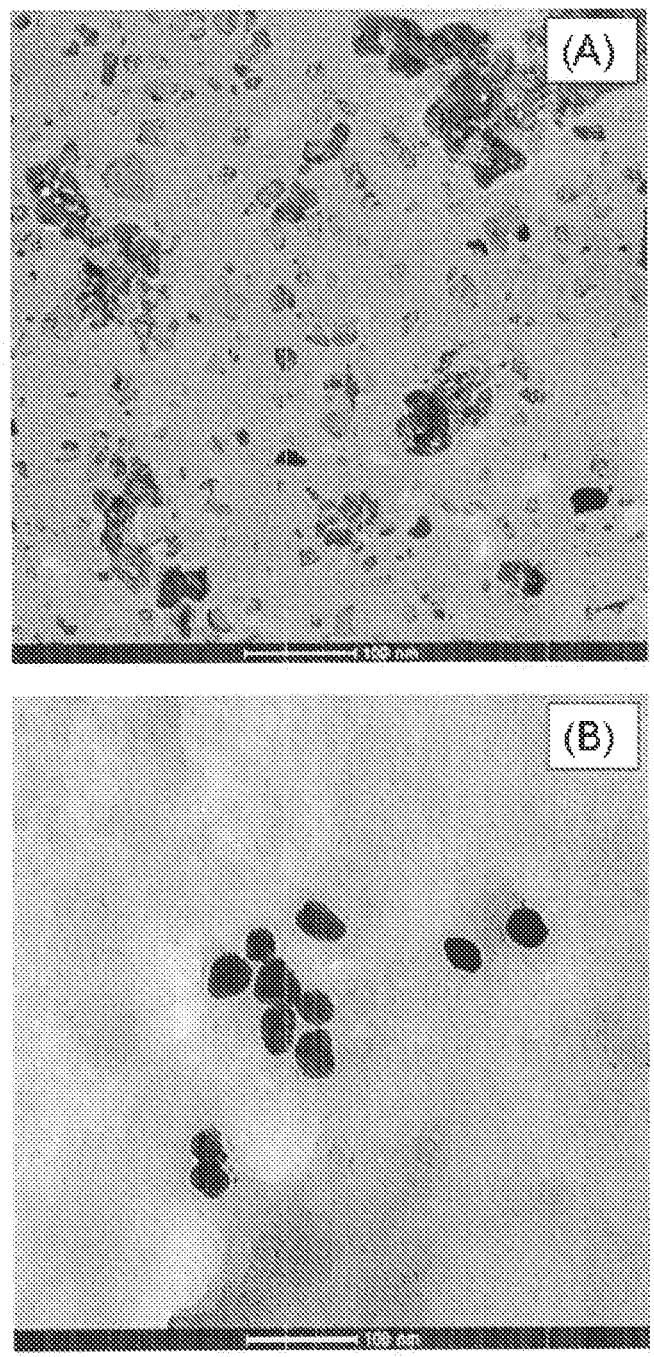
FIGS. 4A and 4B show a representative TEM image of as-purchased $Y_2O_3$ nanoparticles and a representative TEM image for $Y_2O_3$ particles coated with a gold shell using the synthetic procedure described herein, respectively.

Transmission electron microscopy (TEM) provides additional evidence for the presence of gold-coated $Y_2O_3$ particles. FIG. 4A, for example, shows a representative TEM image of as-purchased $Y_2O_3$ nanoparticles. The particles are quite polydisperse, but exhibit an average diameter of approximately 35 nm. FIG. 4B shows similar images for $Y_2O_3$ particles coated with a gold shell using our synthetic procedure. Like the underlying $Y_2O_3$ cores, the gold-coated yttrium oxide particles are somewhat polydisperse with an average diameter of approximately 50 nm.

Figure 5:
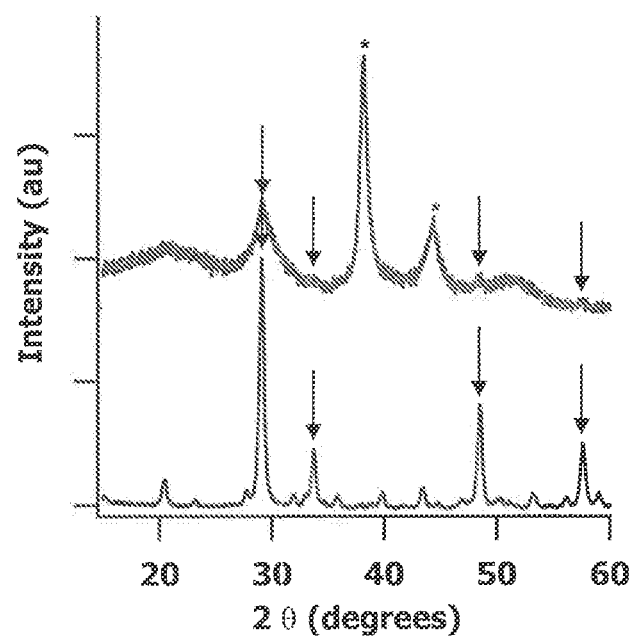
FIG. 5 shows diffractograms for both the initial cubic $Y_2O_3$ nanoparticles (lower trace) and the final gold-coated core-shell particles (upper trace).

Perhaps the most conclusive demonstration that these nanoparticles are in fact gold-coated $Y_2O_3$ comes from comparison of XRD data. FIG. 5 shows diffractograms for both the initial cubic $Y_2O_3$ nanoparticles (lower trace) and the final gold-coated core-shell particles (upper trace). Strong peaks at 2θ=29, 33.7, 48.5 and 57.5 degrees in the lower trace are indicative of cubic $Y_2O_3$. The most pronounced features in the upper trace are two gold-associated peaks at 2θ=38.2 and 44.4 degrees. In addition, the four strongest cubic $Y_2O_3$ peaks at 2θ=29, 33.7, 48.5 and 57.5 degrees are also visibly superimposed on the baseline diffractogram from the gold nanoshells. The reason for the broadening of the $Y_2O_3$ peak at 2θ=29 degrees is not definite, but may be a result of gold-$Y_2O_3$ interactions or, alternatively, the preferential size-selection of small $Y_2O_3$ particles during the 8200 RCF centrifugation used to remove large $Y_2O_3$ particles and aggregates.

Characterization of Peptide Binding: The nature of metal-thiol binding in general and gold-thiol binding in particular has been extensively discussed in the literature. Briefly, it has been well established that both thiol and dithiol functional groups rapidly form strong bonds with metallic gold and silver surfaces. These bonds are quite robust, with bond energies around 40 kcal/mol.[140,141] As a result, gold-thiol and silver-thiol linkages are one of the preferred methods for anchoring both chemical and biochemical sensing functionality to noble metal nanoparticles. Our laboratory has previously used this binding chemistry when designing pH-, DNA-, and mRNA-sensitive SERS-active nanoparticles and nanoprobes, as well as for tracking cellular uptake, fate and transport of noble metal nanoparticles.[142-147]

While it is difficult to directly measure the number of peptide molecules anchored to the gold-coated $Y_2O_3$ nanoparticles prior to functionalization with some fluorescent or absorptive label, simple mathematical modeling can be used to predict the maximum number of nuclear targeting peptide molecules which can theoretically anchor to the gold shell. Highly-charged peptides such as the nuclear targeting peptide we have used in this work are known to primarily exist in extended conformations. As a result, such molecules can generally be modeled as jointed chains with some effective length and Gaussian-like movement. As shown in Equation 1, this effective length (R) can be estimated as the product of the size of the individual "links" in the chain (L) and the square root of the number of "links" in the chain (N).

$$R=L*\sqrt{N} \qquad (\text{Eqn. 1})$$

For the TAT sequence used in this work, L=0.5 nm and N=10, giving an estimated effective length R equal to 1.6 nm. If we make the further assumption that the peptide occupies an area defined by a 45 degree cone on the surface of the gold-coated $Y_2O_3$ nanoparticle, the surface area (A) occupied by a single peptide molecule can be estimated using Equation 2.

$$A=(\pi*R^2)/2 \qquad (\text{Eqn. 2})$$

For R=1.6 nm we would estimate that each peptide molecule occupies approximately 4 $nm^2$ on the nanoparticle surface. Since a sphere with a diameter of 50 nm has a surface area of 7850 $nm^2$, the maximum number of peptide molecules which can theoretically bind to a single gold-coated $Y_2O_3$ nanoparticle without inhibiting peptide motion after binding is on the order of 2000 per particle. This theoretical surface density falls within the same order of magnitude as that measured by a variety of groups for short DNA bound to gold nanoparticles or planar gold substrates.[148-151]

With approximately $10^{14}$ nanoparticles per mL as estimated using the average diameter of the $Y_2O_3$ core particles (~35 nm), the density of $Y_2O_3$ (5.1 $g/cm^3$) and the total mass of $Y_2O_3$ initially dispersed in solution (10 mg/mL), the above peptide-per-particle estimate indicates that a maximum of $2\times10^{17}$ TAT molecules must be present in each mL of solution during functionalization for full surface coverage of the gold-coated $Y_2O_3$ nanoparticles. Note that this estimate does not take into account the large fraction of fused particles and aggregates removed by the 8200 RCF centrifugation step, which could reduce the number of TAT molecules needed for full surface coverage. At a concentration of 1 mg/mL, the amount of TAT available during the nanoparticle functionalization step is 0.7 m$\underline{M}$, meaning that there are approximately $4\times10^{17}$ TAT molecules present in each mL of solution during reaction. This is twice the concentration theoretically required for complete surface coverage.

Characterization of Dye Binding: Coupling of NHS-functionalized molecules to primary amines, like the metal-thiol binding chemistry discussed above, is quite robust and has found broad application in a number of fields. In particular, NHS-functionalized fluorescent dyes such as those used in this study are preferred methods for fluorescent labeling of biomolecules such as peptides and proteins. In part, this is because the amide bonds formed when using NHS-based coupling to primary amines are as robust as the amide bonds along the peptide/protein backbone, and would be expected to remain intact for any conditions under which the peptide/protein backbone remains intact. This characteristic in particular makes NHS-based coupling to biomolecules especially attractive.

It is difficult to directly monitor binding of the TAT peptide to the surface of the gold shell using only UV-vis absorption because the absorption spectra of tri-arginine and TAT are both dominated by absorption by the peptide backbone. UV-vis absorption (FIG. 4) or fluorescence measurements (FIG. 5) after functionalization of TAT with various absorptive and fluorescent dye molecules followed by multiple washing steps to remove dissolved and physisorbed dye or dye-peptide conjugates, however, can provide fairly simple confirmation of peptide binding to the gold-coated $Y_2O_3$ nanoparticles.

Figure 6:
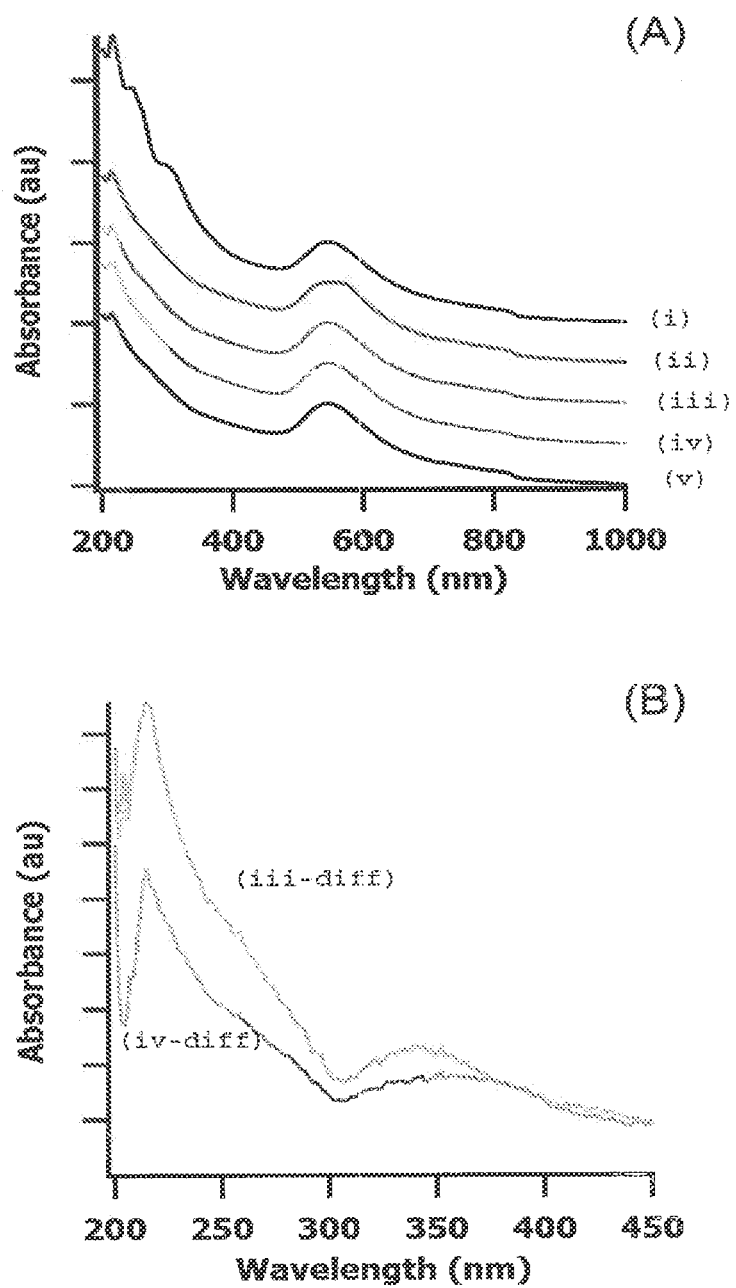
FIGS. 6A and 6B show UV-Vis absorbance spectra for gold-coated $Y_2O_3$ particles before and after functionalization with various dyes.

FIGS. 6A and 6B show UV-Vis absorbance spectra for gold-coated $Y_2O_3$ particles before and after functionalization with various dyes. Absorption by psoralen and Alexa 546 attached to the particle-bound TAT peptide is clearly visible when comparing their absorption spectra (traces (i) and (ii)) to that of the dye-free gold-coated $Y_2O_3$ nanoparticles (trace (v)). Absorption by Marina Blue and Alexa 350 is not obvious in the raw spectra shown in FIG. 4A (traces (iii) and (iv)), but the presence of these dyes can be clearly seen in the difference spectra shown in FIG. 4B following subtraction of the baseline due to the gold-coated $Y_2O_3$ core-shell particles (traces (iii-diff) and (iv-diff)).

Figure 7:
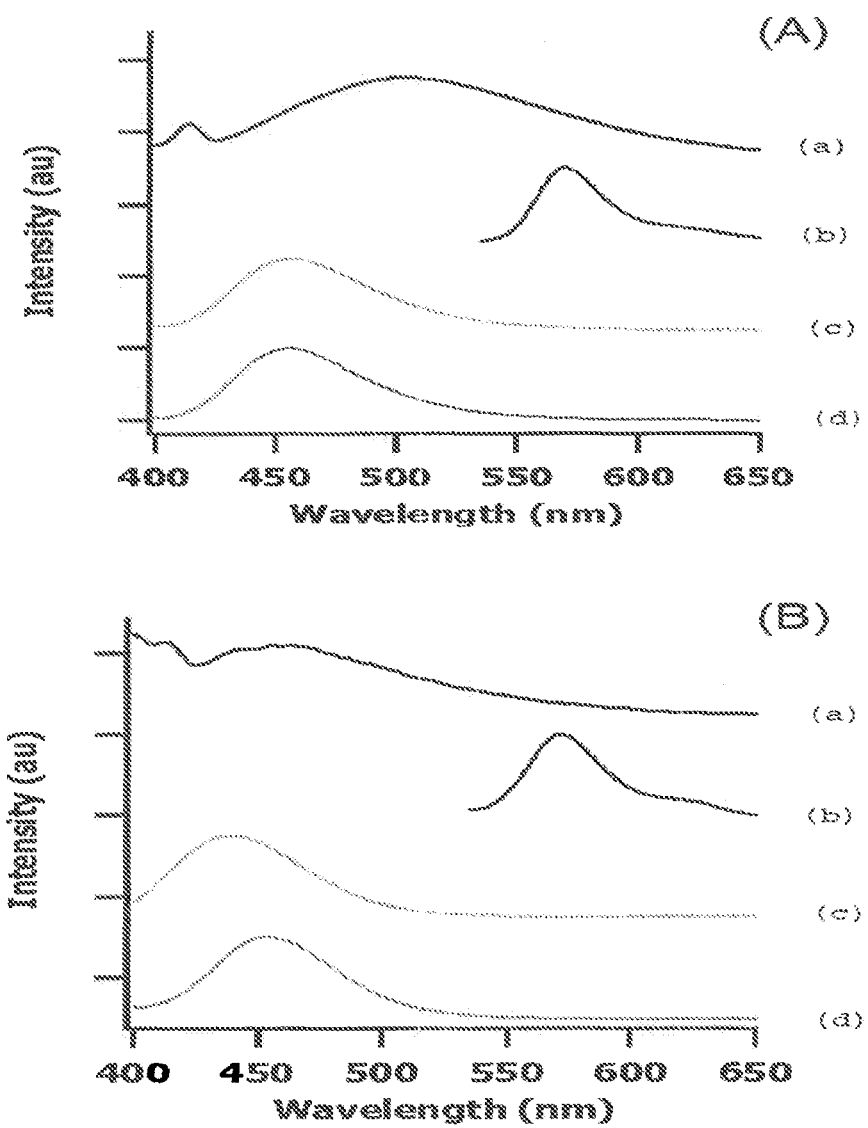
FIGS. 7A and 7B show fluorescence spectra of the free NHS-functionalized dyes (A) and the same dyes attached to TAT tethered to gold-coated $Y_2O_3$ nanoparticles (B).

FIGS. 7A and 7B show fluorescence spectra of the free NHS-functionalized dyes (A) and the same dyes attached to TAT tethered to gold-coated $Y_2O_3$ nanoparticles (B). For unbound dye molecules in the absence of nanoparticles, the fluorescence maxima for Alexa 350 (d), Marina Blue (c), psoralen (a) and Alexa 546 (b) are visible at 455, 458, 503 and 570 nm, respectively. The apparent emission maxima of the dyes shift somewhat following dye attachment to the particle-tethered nuclear targeting peptide, yielding maxima at 454, 439, 462 and 572 nm, respectively. These shifts in the wavelength of maximum fluorescence are most likely due to absorption of emitted photons by gold-coated $Y_2O_3$ nanoparticles between the emitting fluorophores and the detector.

A more definitive means of examining the extent to which the nuclear targeting peptide is functionalized with the various dyes is MALDI-MS. As the binding chemistries for all the NHS esters used in this work are similar, we have used SPB as a model compound when determining binding efficiency. One mg/mL TAT (0.7 mM) was added to 1 mg/mL SPB (2.6 mM) in 10% v/v DMSO, and allowed to react with vigorous stirring in the dark at room temperature. The reaction was quenched with 50 mM L-lysine after one hour to minimize further dye attachment to the targeting peptide after that point in time, and the dye-functionalized peptide was analyzed by MALDI-MS.

Figure 8:
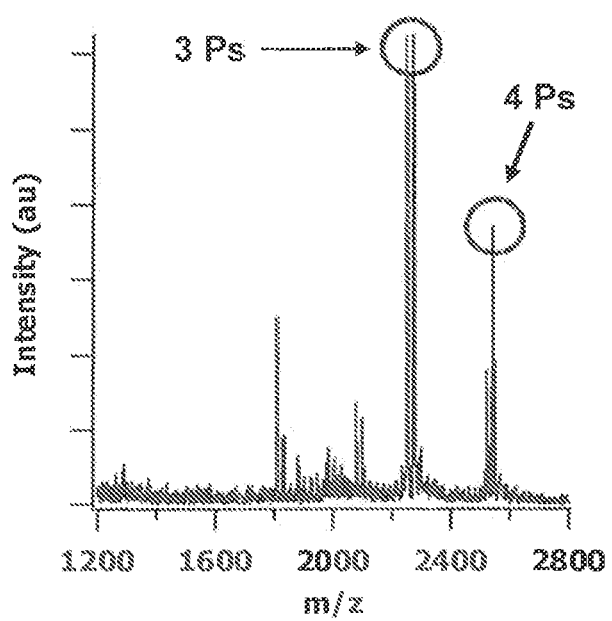
FIG. 8 shows a MALDI-MS spectrum of TAT functionalized as described above, showing strong peaks at m/z=2254/2276, corresponding to peptide functionalized with three psoralen molecules.

FIG. 8 shows a MALDI-MS spectrum of TAT functionalized as described above, showing strong peaks at m/z=2254/2276, corresponding to peptide functionalized with three psoralen molecules. The peak at 2276 is due to peptide molecules which are positively charged due to Na+ rather than H+. The weaker peaks at m/z=2524/2546 are due to peptide molecules which have bound four psoralen molecules. The lack of peaks at m/z=1441/1463 indicates that there are few or no unfunctionalized TAT molecules, highlighting the efficiency of the dye functionalization reaction even under the unoptimized conditions described above.

The functionalized nanoparticles of the present invention most preferably comprise a rare-earth oxide ($Y_2O_3$) core and a noble metal (Au, Ag, etc.) shell, which can be prepared using a simple photochemical method. We have further anchored a cysteine-terminated cell penetrating/nuclear targeting peptide to these nanoparticles, and demonstrated the ability to functionalize the peptide with a variety of fluorescent dyes. The dye molecules retain their ability to fluoresce after attachment to the nuclear targeting peptide anchored to the gold shells, indicating that these hybrid nanoparticles should remain visible within cells when taken up via either endocytosis, phagocytosis, or a combination of these and other cellular uptake processes which may be modulated by the influence of nuclear transport or cell penetrating peptides to aid movement through or across the cell membrane. The details of the cellular uptake mechanism(s) involved in nanoparticle uptake are yet to be elucidated in the scientific literature.

The core of the present invention functionalized nanoparticle preferably has an average diameter of 50 nm or less, more preferably 30 nm or less, most preferably from 5-15 nm. The combination of core and full shell of the present invention preferably has a total average diameter of 50 nm or less, more preferably 30 nm or less, most preferably from 10-15 nm. The average diameter of the nanoparticle can play an important role in getting the functionalized nanoparticle of the present invention into a target cell, particularly into a cancer tumor cell.

Gold Nanoshells for Coating Core The toxicity of energy modulation agent materials is often not known. It is, therefore, desirable to coat the energy modulation agent materials with an inert coating. Gold-coated (or other materials such as silica) nanoparticles (NPs) are good starting candidates for nanoparticles (N)-based drug development. The metal NPs are easy to prepare and the chemistries to bind biomolecules to these materials are well established. Furthermore gold in particular is an inert material that can be conveniently used in animals and humans. Gold nanoparticles are quite inert and have even been suggested for use as a contrast agent in CT imaging. Gold nanoparticles are attractive because gold has been approved and used for treatment of human disease (e.g. rheumatoid arthritis) [Mottram P L. *Past, present and future drug treatment for rheumatoid arthritis and systemic lupus erythematosus. Immunol Cell Biol.*,81:350-353 (20030}

Nuclear Membrane Transport Peptides To develop an effective psoralen-based drug system, it is important that the psoralen molecule enter the cell and preferably the nucleus in order to bind to DNA. We have investigated the use of nuclear membrane transport peptides (NTP) for this purpose, particularly the TAT (48-57) protein. Previous research has shown the usefulness of this NTP approach [Alexander G. Tkachenko, Huan Xie, Donna Coleman, Wilhelm Glomm, Joseph Ryan, Miles F. Anderson, Stefan Franzen, and Daniel L. Feldheim, *Multifunctional Gold Nanoparticle-Peptide Complexes for Nuclear Targeting, J. Am. Chem. Soc.*, 2003, 125 (16), pp 4700-4701]

A preferred embodiment of the present invention shows that TAT-functionalized UVA-scintillating nanoparticles further functionalized with psoralen show some X-ray activated efficacy against human cancer cell lines. The literature lists a number of potentially useful peptides, each of which could be used in the present invention [Ref: *Handbook of Cell-Penetrating Peptides*, Ulo Langel (ed.), $2^{nd}$ edition, Taylor and Francis, New York, N.Y., 2007]

The most well-characterized of the cell penetrating/nuclear transport peptides are the transactivator of HIV transcription (Tat) peptide, Antennapedia (Antp), Herpes simplex virus (HSV-1) type 1 protein (VP22), transportan, penetratin, model amphipathic peptide (MAP), engineered polyarginines, and selectively substituted polyarginines Other peptide sequences have shown potential, as well. TAT (48-57) is the most heavily investigated, but all of these sequences have demonstrated the ability to travel into the cytosol and many have shown potential as nuclear targeting domains. The activity and behavior of any particular cell-penetrating/nuclear transport peptide appears to vary somewhat as a function of cell line and cargo.

Figure 9:
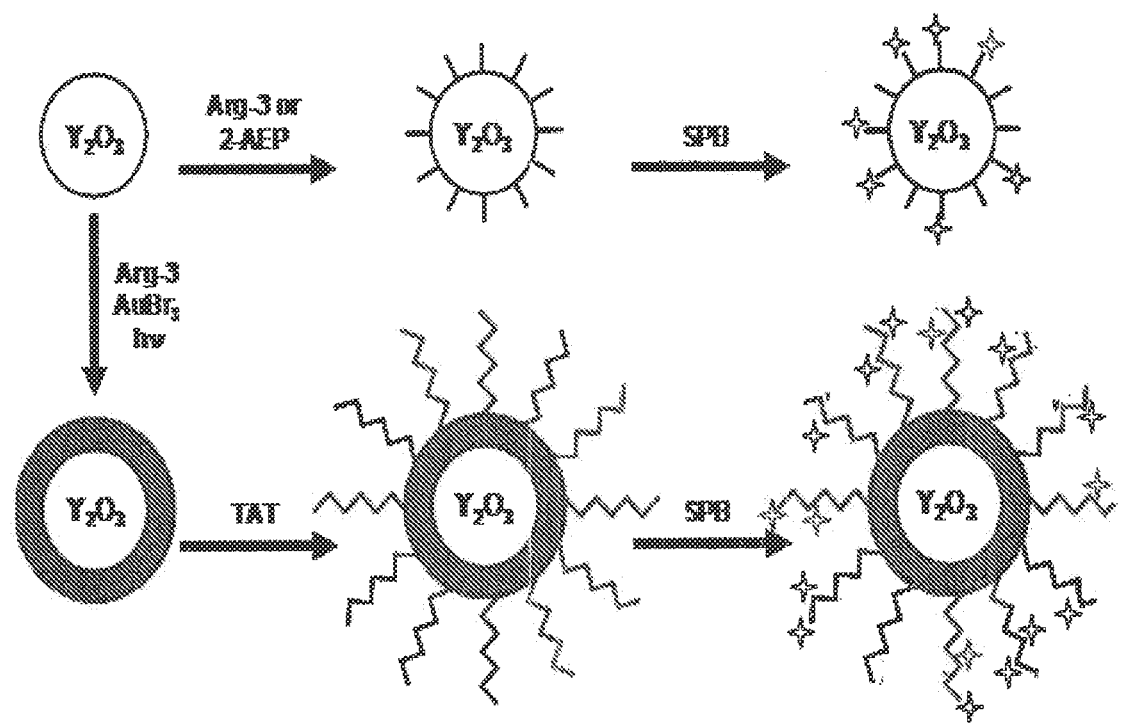
FIG. 9 shows two examples of structures fitting within a broader class of psoralen-linked nanoparticle materials.

Development of psoralen-linked nanoparticles FIG. 9 shows two examples of structures fitting within this broader class of potential materials. The first has no shell because the X-ray luminescent nanoparticles are either minimally toxic or inherently non-toxic. The second has an inert shell (e.g., gold) to improve biological compatibility and/or reduce toxicity in the case of intrinsically-toxic scintillating nanomaterials. In this particular work, we have used commercially available $Y_2O_3$ nanoparticles modified with psoralen-functionalized Arg-Arg-Arg-OH (tri-arginine), and $Y_2O_3$ coated with a nanometers-thick gold shell modified with a psoralen-functionalized, thiolated version of the HIV TAT peptide (residues 48-57, sequence Arg-Lys-Lys-Arg-Arg-Arg-Gln-Arg-Arg-Cys-$CONH_2$, molecular weight 1442 g/mol, hereafter referred to as "TAT"). Both $Y_2O_3^N$ and this particular segment of $TAT^O$ have been shown to be non-toxic, thereby making this specific nanomaterial-peptide-psoralen formulation a preferred first-generation drug.

Figure 10:
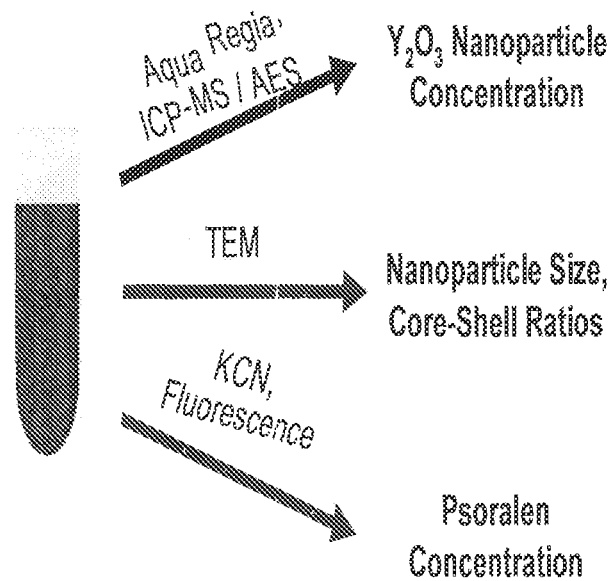
FIG. 10 illustrates procedures that can be used for quantitative determination of psoralen bound to gold-coated $Y_2O_3$ nanoparticles

FIG. 10 illustrates procedures that can be used for quantitative determination of psoralen bound to gold-coated $Y_2O_3$ nanoparticles Fabrication of $Y_2O_3$ nanoparticles functionalized with psoralen is a relatively straightforward process. As discussed in the literature, the surface-associated $CO_2$ typically present on cubic-phase $Y_2O_3$ after annealing can be displaced by both carboxylic and phosphonic acids.[P] The proper choice of surface modifier depends on the next step in the particle functionalization process. If strong, semi-permanent bonds with the $Y_2O_3$ surface are required, then phosphonic acids appear to be nearly ideal. If the particle surface is to be further coated with $SiO_2$, Au, Ag, etc., however, we have found that carboxylic acids (such as short peptides, for example) are preferable to phosphonic acids due to the weaker nature of the carboxylic acid-$Y_2O_3$ interaction and the ease with which carboxylic acids can be displaced from the $Y_2O_3$ surface. As an added benefit, a carefully-chosen carboxylic acid can actively assist in formation of gold, silver, silica, etc. shells on the $Y_2O_3$ core particles.

As an example, we have developed a photochemical procedure in which tri-arginine acts as both a nanoparticle dispersant and a reactant when coating gold shells on $Y_2O_3$. Briefly, 10 mM tri-arginine (Bachem, Torrance, Calif.) dissolved in sterile water for injection (SWFI, EMD Chemicals, Gibbstown, N.J.) and filtered at 0.22 microns is added to dry, autoclaved $Y_2O_3$ nanoparticles (Nanostructured and Amorphous Materials, Los Alamos, N. Mex. and Meliorum Technologies, Rochester, N.Y.) to yield a final particle concentration of 10 mg/mL. The mixture is ultrasonicated for 30 minutes, and the resulting solution is moderately stirred in a sealed, autoclaved glass bottle for 24 hours. Large agglomerates and fused aggregates from the annealing process are removed by centrifugation at 8200 RCF for three minutes, and the centrifugate is combined with a 1:1 volume of 5.7 mM gold tri-bromide ($AuBr_3$, 99.99% purity, Alfa Aesar, Ward Hill, Mass.) dissolved in SWFI and sterile filtered at 0.22 microns. Within seconds of mixing, the dark red-brown color from the $AuBr_3$ disappears and the solution turns to a pale yellow. This solution is then exposed to high-intensity fluorescent light for a minimum of 16 hours at room temperature, during which the pale yellow color is replaced by a deep purple. This nanoshell-containing solution is characterized by strong absorption at ~546 nm, which is indicative of the presence of gold nanoshells around $Y_2O_3$ cores. Combination of tri-arginine and $AuBr_3$ in the absence of $Y_2O_3$ also produces a pale yellow initial solution, but the final solution remains clear and colorless after exposure to fluorescent light at room temperature.

Following attachment of gold nanoshells to the $Y_2O_3$ cores, further functionalization with the thiol-modified nuclear transport peptide simply requires particle purification via triplicate centrifugation at ~16 k RCF with redispersion in SWFI, followed by final redispersion in a 1 mg/mL solution of sterile-filtered TAT (SynBioSci, Livermore, Calif.) dissolved in SWFI. This solution is reacted at room temperature for two hours with moderate mixing, after which the TAT-functionalized, gold-coated $Y_2O_3$ nanoparticles are purified by triplicate centrifugation with final redispersion in sterile filtered 5 wt % dextrose (Mallinckrodt Baker, Phillipsburg, N.J.) prepared using SWFI. These psoralen-free, TAT-functionalized particles are used as a control to ensure that enhanced ROS generation due to X-ray interaction with the gold nanoshells does not result in visibly increased cell death. Such increases in ROS-induced cell death can partially or completely mask cell death due to psoralen activation by the UVA-emitting $Y_2O_3$ nanoparticles and, if present, would lead to significant artifacts during qualitative examination of drug activation.

Psoralen (or a psoralen derivative) can be added to the TAT-functionalized gold-coated $Y_2O_3$ nanoparticles by reacting succinimidyl-[4-(psoralen-8-yloxy)]butyrate (SPB, Pierce, Rockford, Ill.) with the thiol-tethered targeting peptide. SPB is a N-hydroxysuccinimide ester of psoralen which efficiently attaches psoralen to primary amines such as the lysine side-chains and N-terminus of TAT. We use typical NHS ester functionalization conditions when conjugating psoralen to the nanoparticle-TAT complex, with 100 microliters of 10 mg/mL SPB in endotoxin-free DMSO (Sigma-Aldrich, St. Louis, Mo.) added to each mL of nanoparticles and allowed to react in the dark at room temperature with moderate mixing for one hour. The drug-functionalized nanoparticles are centrifuged once at 16 k RCF, and washed with 25% v/v DMSO to remove any unbound SPB. The particles are then centrifugally cleaned three times with SWFI to remove the DMSO, and finally redispersed in sterile filtered 5 wt % dextrose for addition to cell cultures.

Fabrication of $Y_2O_3$ particles with psoralen attached via reaction of SPB with either amine-terminated phosphonic acids or tri-arginine uses a procedure similar to that described above. The primary differences are that the particles lack a gold shell, and they do not have a transport peptide attached to their surface.

Demonstration of cellular activity of psoralen-linked nanoparticles on cancer cells using X-ray activation During in vitro testing, a small volume of the purified nanoparticle solution is added to PC-3 cells plated in six-well culture plates 24 hours prior to treatment. The cells are allowed several hours for nanoparticle uptake and transport to the nucleus, at which time the cultures are exposed to UVA light (Stratagene, Garden Grove, Calif.) or X-ray radiation (Pantax). The culture media is changed immediately after UV or X-ray exposure, and the cultures are incubated under standard conditions.

Figure 11:
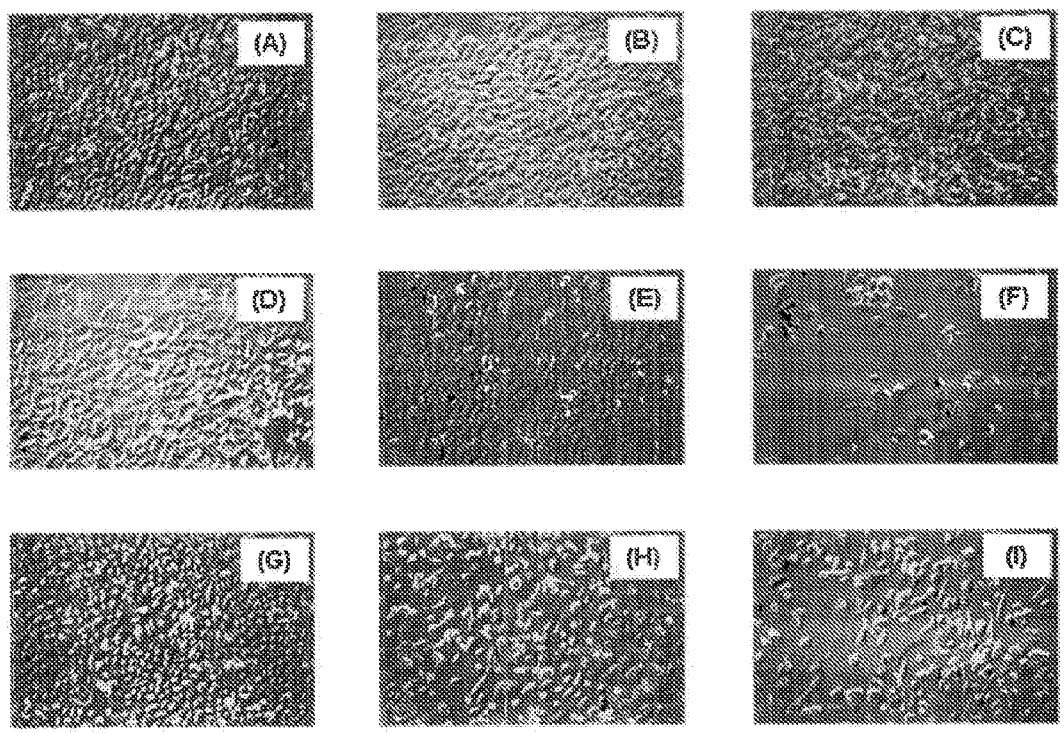
FIGS. 11A-11I show representative images for cell cultures using gold-coated $Y_2O_3$ nanoparticles functionalized with psoralen attached to the particle surface via TAT with various conditions.

Comparison of cell density in treated+irradiated cell cultures and control cultures several days after treatment provides a qualitative measure of the extent to which drug activation is reducing cell growth rates or, in the ideal case, inducing cell death. Similar techniques (such as cell density measurement following MTT or WST staining) are routinely used as a "first pass" when examining toxicity or chemotherapeutic efficacy. FIG. 5 shows representative images demonstrating the difference in cell density for drug-functionalized $Y_2O_3$ nanoparticles exposed to X-ray radiation versus positive and negative control cultures, and FIG. 11 shows representative images for the case of gold-coated $Y_2O_3$ nanoparticles functionalized with psoralen attached to the particle surface via TAT. While qualitative in nature, these in vitro results provide an indication of the potential for activation of particle-tethered psoralen by UV light and/or X-ray radiation.

As shown in FIGS. 11A through 11C, the mere presence of $Y_2O_3$ or psoralen-functionalized $Y_2O_3$ does not appear to affect cell density in the absence of UV light or X-ray radiation. This finding is consistent with the use of $Y_2O_3$ in digestive studies[S] and with past reports indicating that the material is intrinsically non-toxic.[T] Some decrease in cell density is evident when cells are treated with $Y_2O_3$ nanoparticles and exposed to either UV light or X-ray radiation (FIGS. 11E and 11H). The fundamental biological source of these reductions in cell density cannot be determined based on the current results because simple number density measurements, like clonogenic experiments, are unable to provide a biomolecular context for reduced rates of cell growth or increased rates of cell death. More recent experiments using lower concentrations of $Y_2O_3$ nanoparticles have shown no appreciable increases in cell death due to UV or X-ray exposure in the absence of psoralen. As a result, it may be that the reduced cell densities in the UV and X-ray control cultures are a result of direct UV and X-ray interaction (heating, ROS generation, etc.) with the large amount of $Y_2O_3$ nanoparticles used in our initial experiments (100 µg/mL).

When PC-3 cell cultures containing psoralen-functionalized $Y_2O_3$ nanoparticles are exposed to UV light or X-ray radiation, an additional reduction in cell density becomes apparent (FIGS. 11F and 11I). As noted above, the source of these reductions in cell density cannot be definitively determined by the current round of experiments, but it would seem reasonable to conclude that the lack of direct toxicity associated with the psoralen-functionalized $Y_2O_3$ nanoparticles themselves would remain self-consistent, as would any activity associated with direct interactions of $Y_2O_3$ and UV light or X-ray radiation. As a result, the observed reductions in cell density may be related to the combined effects of UV or X-ray exposure and activation of psoralen tethered to $Y_2O_3$.

The distinction between UV-particle or X-ray particle interactions and psoralen activation is much more clear-cut for the case of gold-coated $Y_2O_3$ nanoparticles functionalized with psoralen via the TAT peptide. FIGS. 12A through 12C show representative images of PC-3 cells not exposed to nanoparticles or psoralen (A), PC-3 cells treated with gold-coated $Y_2O_3$ nanoparticles lacking tethered psoralen (B), and PC-3 cells treated with psoralen-functionalized gold-coated $Y_2O_3$ (C). No appreciable reduction in cell density is visible when comparing these control cultures, indicating a lack of substantial intrinsic toxicity in the absence of UV light or X-ray radiation. Cell density remains self-consistent for cell cultures illuminated with UV light in the presence and absence of psoralen-free gold-coated $Y_2O_3$ nanoparticles (FIGS. 12D and 12E). Cell density falls precipitously in PC-3 cultures treated with psoralen-functionalized gold-coated $Y_2O_3$ exposed to UV light, a finding which is consistent with psoralen activation in the normal manner. Cell exposure to 2 Gy X-ray radiation appears to cause minor reductions in cell density in both the presence (FIG. 12G) and absence (FIG. 12H) of gold-coated $Y_2O_3$ nanoparticles when compared to control cultures (FIGS. 12A and 12B). Cell cultures treated with psoralen-functionalized gold-coated $Y_2O_3$ nanoparticles show an additional decrease in cell density upon exposure to 2 Gy X-ray radiation when compared to X-ray and particle+X-ray controls. Given that the psoralen-functionalized nanoparticles themselves display minimal toxicity in the absence of UV or X-ray activation, given that the $Y_2O_3$ cores emit UVA light, and given that UVA light is known to be the traditional means of psoralen activation, it appears possible that UVA photons emitted by the gold-coated $Y_2O_3$ nanoparticles may be activating psoralen.

Figure 12:
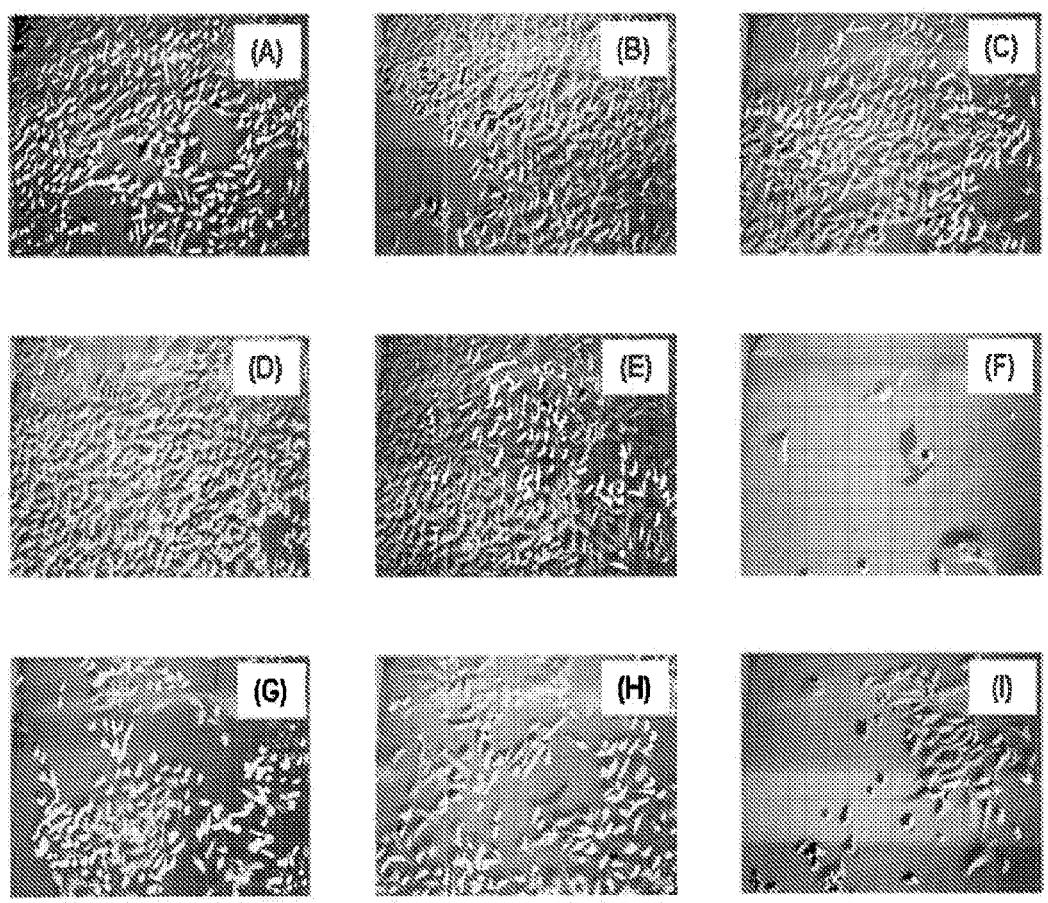
FIGS. 12A-12I show representative images of tests on PC-3 cells under various conditions.
Figure 13:
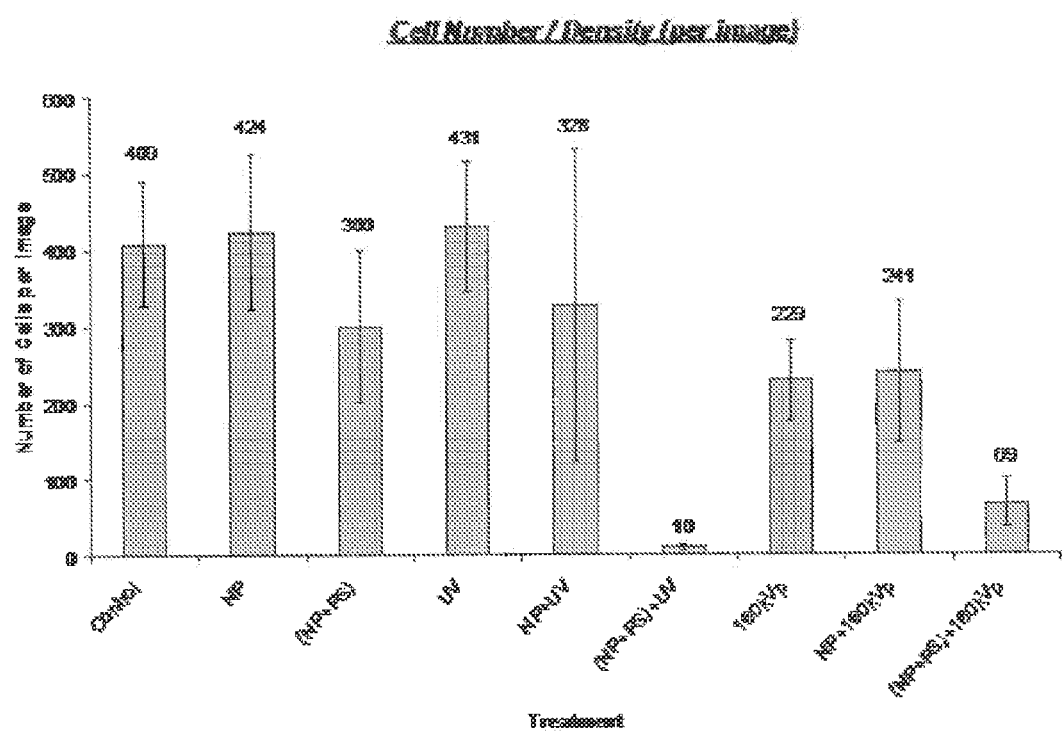
FIG. 13 shows quantitative results from cell number/density measurements of images similar to those in FIGS. 12A-12I.

FIG. 13 shows quantitative results from cell number/density measurements of images similar to those in FIG. 12, produced by counting the number of cells in the field of view for 10 separate images at each experimental condition. Error bars correspond to one standard deviation.

Figure 14:
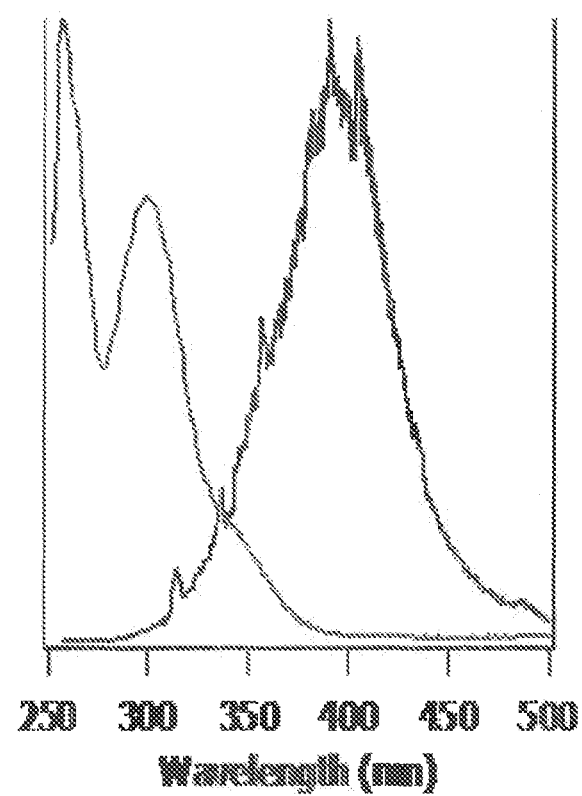
FIG. 14 shows absorption spectra to show how the X-ray excited nanoparticle luminescence spectrum (right hand trace) at least partially overlaps the psoralen absorption spectrum (left hand trace).

As with more traditional light-activated therapies based on energy transfer, it is essential that the X-ray excited nanoparticle luminescence spectrum (right hand trace) at least partially overlaps the psoralen absorption spectrum (left hand trace) as shown in FIG. 14. This fundamental requirement, of course, indicates that many scintillators will be inappropriate for psoralen activation (in large part because most of them have been developed for optimal detection by silicon-based detectors,[K] whose greatest sensitivity is in the green and red portions of the visible spectrum). The range of suitable materials for in vitro and in vivo use is further limited by the requirement that the scintillating nanoparticles not be water-soluble, as scintillators lose their X-ray optical luminescence upon dissolution. Lack of toxicity is also desirable, but is not necessarily critical if the scintillating nanoparticles are only slightly toxic or can be covered with some optically transparent coating which is impermeable to toxins.

TABLE 1

Several UVA-emitting scintillating nanoparticles.

| Material | λ(max) (nm) | photons per MeV at 662 keV | Weaknesses | Ref |
|---|---|---|---|---|
| CeBr3 | 371 | 68000 | WS | AA |
| CeCl3 | 350 | 46000 | WS | AB |
| GdAlO3: Ce | 335-360 | 9000 | NCN | AC |
| K2CeCl5: Ce | 370 | 30000 | WS | AD |
| K2LaBr5: Ce | 355-390 | 40000 | WS | AE |
| K2LaCl5: Ce | 340-375 | 39650 | WS | AF |
| K2LaI5: Ce | 340-380 | 29000 | WS | AG |
| KYP2O7: Ce | 380 | 10000 | NCN | AH |
| LaBr3: Ce | 355-390 | 67500 | WS | AI |
| LaCl3: Ce | 330-355 | 49000 | WS | AJ |
| LuAlO3: Ce | 365 | 16350 | NCN | AK |
| LuPO4: Ce | 360 | 17200 | NCN | AL |
| PbSO4 | 340-380 | 10000 | TX | AM |
| PrBr3: Ce | 365-395 | 21000 | NCN, WS | AN |
| Y2O3 | 370 | 15480 | — | AO |
| YAlO3: Ce | 345-365 | 18360 | NCN | AP |

Light yield (photons per MeV of absorbed X-ray radiation) at 662 keV describes how efficiently each material converts X-ray photons into UVA photons. WS = water soluble, NCN = No commercially-available nanoparticles. TX = toxic.

Table 1 lists a small subset of the UVA-emitting scintillators which have potential as psoralen activators.[L] Several of these materials such as cubic $Y_2O_3$, $LaBr_3$:Ce, etc. are either commercially available as nanoparticles or can be easily synthesized in the laboratory using published methods.[M] Others, such as the cerium-doped perovskites $YAlO_3$:Ce and $LuAlO_3$:Ce, are less immediately available as nanoparticles but may be superior psoralen excitation sources depending on the quantum efficiency with which they down-convert X-ray photons to UVA photons. Many of the most efficient scintillators are unfortunately highly hygroscopic or water soluble, but this weakness may potentially be overcome by encasing them in a water-tight shell.

These cell density results provide evidence that psoralen tethered to scintillating nanoparticles is useful for treating tumor cells and ultimately assisting in the fight against cancer. In particular, with the use of X-ray radiation, such a particle-psoralen configuration has unique potential as a non-invasive anti-cancer treatment modality for deep-tissue tumors in hypoxic environments, due to their ability to inhibit cell growth and/or induce apoptosis.

The functionalized nanoparticles of the present invention can be incorporated into pharmaceutical compositions suitable for administration. Such compositions typically comprise the functionalized nanoparticles and a pharmaceutically acceptable carrier. The pharmaceutical composition can optionally comprises one or more additives having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Alternatively, combined therapies (e.g., NP+Psoralen and chemotherapy; NP+Psoralen and hyperthermia, NP+Psoralen and regular radiation therapy, etc) can also be used. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens or liposmes with bioreceptors targeted to tumor cells) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, kit or dispenser together with instructions for administration.

In using the present invention functionalized nanoparticle for treatment of a cell proliferation disorder such as cancer, the treatment can be a single treatment (combination of administration of the functionalized nanoparticle and application of X-rays), or can be a series of treatments (where each separate treatment can include both administration of the functionalized nanoparticle and application of X-rays, or the first treatment and any subsequent treatment may include administration of functionalized nanoparticle, while applying X-rays at intervals as desired, such as 1-4 treatments per day for a period of 5-15 days). The total X-ray dosage is preferably from 1-4 Gy per application, with more preference given to the lower doses of X-ray to avoid damage to target or non-target cells due to the X-rays themselves.

In a further embodiment, the nanoparticle comprising the energy modulation agent core and a shell has a Protein Transduction Domain (PTD), or cell-penetrating peptide (CPP) attached to the shell to aid the composition to gain access to the interior of the target cell or nucleus. Nuclear Transporting Peptides (NTPs) are CPPs that allow intracellular transport of drug systems inside the nucleus.

A wide variety of peptides are usable, including, but not limited to, Antennapedia (Antp) [A. Joliot, C. Pernelle, H. Deagostini-Bazin, A. Prochiantz, *Antennapedia homeobox peptide regulates neural morphogenesis*, Proc. Natl. Acad. Sci. USA 88 (1991) 1864-1868], VP22 [G. Elliott, P. O'Hare, *Intercellular trafficking and protein delivery by a herpesvirus structural protein*, Cell 88 (1997) 223-233.], transportan [M. Pooga, M. Hallbrink, M. Zorko, U. Langel, *Cell penetration by transportan*, FASEB 1 12 (1998) 67-77.], model amphipathic peptide MAP [J. Oehlke, et al., *Cellular uptake of an alpha-helical amphipathic model peptide with the potential to deliver polar compounds into the cell interior non-endocytically*, Biochim. Biophys. Acta 1414 (1998) 127-139.], signal sequence-based peptides [M Rojas, J. P. Donahue, Z. Tan, Y. Z. Lin, *Genetic engineering of proteins with cell membrane permeability*, Nat. Biotechnol. 16 (1998) 370-375.], and synthetic polyarginines [S. Futaki, et al., *Arginine-rich peptides. An abundant source of membrane-permeable peptides having potential as carriers for intracellular protein delivery*, J. Biol. Chem. 276 (2001) 5836-5840.]

A more preferred CPP is the TAT peptide (TATp), which is derived from the transcriptional activator protein encoded by human immunodeficiency virus type 1 (HIV-1) [K. T. Jeang, H. Xiao, E. A. Rich, *Multifaceted activities of the HIV-1 transactivator of transcription, Tat*, J. Biol. Chem. 274 (1999) 28837-28840.]. The transduction ability of Tat protein is due to the positive charge in the transduction domain of TAT (TATp), which extends from residues 47-57: Tyr-Gly-Arg-Lys-Lys-Arg-Arg-Gln-Arg-Arg-Arg, which contains six arginines (Arg) and two lysine residues [S. R. Schwarze, K. A. Hruska, S. F. Dowdy, Protein transduction: unrestricted delivery into all cells? Trends Cell Biol. 10 (2000) 290-295.]

Other CPP systems that can be used in the present invention include, but are not limited to, MAP, transportan, TATp (48-60), and penetratin. Similarly, MAP has the highest cargo delivery efficiency, followed by transportan, TATp (48-60), and penetratin. For a review, see Ref [Vladimir P. Torchilin, *Tat peptide-mediated intracellular delivery of pharmaceutical nanocarriers*, Advanced Drug Delivery Reviews 60 (2008) 548-558, and reference therein]

EXAMPLES

Materials:

Yttrium oxide nanoparticles were purchased from Nanoscale and Amorphous Materials, Inc. (Los Alamos, N. Mex.) or Meliorum Technologies, Inc. (Rochester, N.Y.). Tri-arginine (H-Arg-Arg-Arg-OH) acetate was purchased from Bachem (Torrance, Calif.), and gold tribromide ($AuBr_3$) was purchased from Alfa Aesar (Ward Hill, Mass.). Dimethyl sulfoxide (DMSO) was purchased from CalBioChem (La Jolla, Calif.) and was used as received. A cysteine-modified version of the TAT peptide (residues 49-57, sequence Arg-Lys-Lys-Arg-Arg-Arg-Gln-Arg-Arg-Cys-$CONH_2$, molecular weight 1442 g/mol, hereafter referred to as "TAT") was custom-synthesized by SynBioSci (Livermore, Calif.). Succinimidyl-[4-(psoralen-8-yloxy)]butyrate (SPB) was purchased from Pierce (Rockford, Ill.), and Marina Blue, Alexa 350 and Alexa 546 NHS esters were purchased from Invitrogen (Carlsbad, Calif.). Ultrapure 18.2 MΩ deionized (DI) water purified with a Millipore Synergy filtration system (Millipore, Billerica, Mass.) was used to make all solutions.

Yttrium Oxide Dispersion: Tip sonication was used to disperse autoclaved $Y_2O_3$ nanoparticles at 10 mg/mL in 10 mM tri-arginine solution which had been pre-filtered at 0.22 microns. Following moderate mixing in a sealed, sterile container on a stir plate for 24 hours to allow tri-arginine attachment and improved $Y_2O_3$ dispersion, the solution was centrifuged at 8200 RCF to remove fused particles and large aggregates.

Gold Shell Formation: Supernatant from the initial $Y_2O_3$ dispersion was diluted 1:1 (v/v) with 5.7 mM $AuBr_3$ dissolved in sterile DI water and pre-filtered at 0.22 microns, then exposed to high-intensity fluorescent light (Commercial Electric, Model 926) for 16 hours in a sealed, sterile glass container with moderate mixing. During the time course of this photochemical process the reddish-brown $AuBr_3$ solution turns yellow immediately after addition of the $Y_2O_3$ in tri-arginine; becomes clear and visually colorless; then develops an intense purple color as Au shells form on the $Y_2O_3$ cores. In the absence of the $Y_2O_3$ cores, neither the intense purple color associated with plasmonic absorption by gold nanoshells nor the deep red color associated with solid gold nanoparticles appears. Use of heat rather than light in the presence of $Y_2O_3$ particles tends to produce a large number of solid gold nanoparticles rather than or in addition to core-shell structures, as evidenced by strong absorption at ~530 nm.

Particle Functionalization with TAT: Gold-coated $Y_2O_3$ nanoparticles were centrifuged at 16 k RCF for 15 minutes, and the pellet was re-dispersed in a 50% volume of sterile DI water by brief tip sonication. The particles were further purified by two additional centrifugations at 16 k RCF for 15 minutes each, with re-dispersion in a 100% volume of sterile DI water following the second centrifugation and final re-dispersion in a 100% volume of 1 mg/mL (0.7 mM) TAT peptide dissolved in sterile DI water and pre-filtered at 0.22 microns.

This solution was vigorously mixed at room temperature for one hour to allow thiol anchoring to the gold shell via the c-terminal cysteine residue.

Peptide Functionalization with Dye Molecules: The TAT-functionalized, gold-coated $Y_2O_3$ particles were purified by triplicate centrifugation at 16 k RCF, with the first two re-dispersions in sterile DI water and the final re-dispersion in sterile 100 mM bicarbonate buffer at pH 9.0. Each NHS ester (SPB, Alexa 350, Marina Blue and Alexa 546) was dissolved at 10 mg/mL in DMSO, and 100 microliters of a given NHS-fuctionalized dye was added to a 1 mL aliquot of TAT-functionalized, gold-coated $Y_2O_3$. The solutions reacted for one hour at room temperature in the dark with vigorous mixing to allow attachment of dye molecules to primary amines along the TAT peptide (such as the N terminus and the lysine side chains).

The psoralen-functionalized nanoparticles were centrifugally cleaned using a 1:1 volume of DMSO in water to remove any residual SPB crystals, then all dye-functionalized core-shell nanoparticles were purified by triplicate centrifugation at 16 k RCF for 15 minutes. Each centrifugation step was followed by re-dispersion in a 100% volume of sterile DI water. Presuming removal of 95+% of non-attached dye molecules during each centrifugation step, we estimate that no more than 0.01% of the unbound dye remains in the final solution.

Nanoparticle Characterization: A variety of techniques were used to characterize the gold-coated $Y_2O_3$ over the course of the fabrication process. UV-visible absorption spectra were collected from 200 to 1000 nm using a Shimadzu UV-3600 UV-Vis-NIR dual-beam spectrophotometer (Shimadzu Scientific Instruments, Columbia, Md.) and fused silica or methacrylate cuvettes with a 1 cm path length. Solutions were typically diluted by a factor of 10 with DI water prior to spectral acquisition. Fluorescence spectra for solutions of dye-functionalized nanoparticles diluted by a factor of 100 with DI water were acquired using a Fluorolog 3 fluorimeter (Horiba Jobin Yvon, Edison, N.J.) and fused silica cuvettes with a 1 cm path length. X-ray diffraction (XRD) measurements were performed on dry powders using a Philips X'Pert PRO MRD HR X-Ray Diffraction System (PANalytical Inc., Westborough, N.J.) with a Cu K-α source powered at 45 kV and 40 mA. A ½ degree slit was typically used, and the beam was apertured to match the sample size. All transmission electron microscopy (TEM) images were collected using a FEI Tecnai $G^2$ Twin (FEI Company, Hillsboro, Oreg.) operated at 160 kV. Matrix-assisted laser desorption and ionization—mass spectrometry (MALDI-MS) data was collected using a Voyager-DE Pro Biospectrometry workstation equipped with a nitrogen laser operating at 337 nm (Applied Biosystems, Foster City, Calif.).

Obviously, numerous modifications and variations of the present invention are possible in light of the above teachings. It is therefore to be understood that within the scope of the appended claims, the invention may be practiced otherwise than as specifically described herein.

REFERENCES

A. Jemal, A.; Thun, M. J.; Ries, L. A. G.; Howe, H. L.; Weir, H. K.; Center, M. M.; Ward, E.; Wu, X-C.; Eheman, C.; Anderson, R.; Ajani, U. A.; Kohler, B.; Edwards, B. K. *J. Natl Cancer Inst* 2008, 100(23), 1672-1694.
   a. World Health Organization, World Cancer Report 2003.
B. Brigger, I.; Dubernet, C.; Couvreur, P. *Adv. Drug Delivery Rev.* 2002, 54, 631-651.
   a. Yih, T. C.; Wei, C. *Nanomed. Nanotechnol. Biol. Med.* 2005, 1, 191-192.
   b. Yezhelyev, M. V.; Gao, X.; Xing, Y.; Al-Hajj, A.; Nie, S.; O'Regan, R. *Lancet Oncol* 2006, 7, 657-667.
   c. Cuenca, A. G.; Jiang, H.; Hochwald, S. N.; Delano, M.; Cance, W. G.; Grobmyer, S. R. *Cancer* 2006, 107, 459-466.
   d. Gu, F. X.; Karnik, R.; Wang, A. Z.; Alexis, F.; Levy-Nissenbaum, E.; Hong, S.; Langer, R. S.; Farokhzad, O. C. *Nanotoday* 2007, 2(3), 14-21.
   e. Huang, X.; Jain, P. K.; El-Sayed, I. H.; El-Sayed, M. A. *Nanomedicine* 2007, 2(5), 681-693.
C. Gulyaev, A. E.; Gelperina, S. E.; Skidan, I. N.; Antropov, A. S.; Kivman, G. Y.; Kreuter, J. *Pharm. Res.* 1999, 16(10), 1564-1569.
   a. Alexiou, C.; Jurgons, R.; Schmid, R.; Hilpert, A.; Bergemann, C.; Parak, F.; Iro, H. *J. Magn. Magn. Mater.* 2005, 293, 389-393.
   b. Song, M.; Wang, X.; Li, J.; Zhang, R.; Chen, B.; Fu, D. *J. Biomed. Mater. Res.* 2007, 86A, 942-946.
   c. Nystrom, A. M.; Xu, Z.; Xu, J.; Taylor, S.; Nittis, T.; Stewart, S. A.; Leonard, J.; Wooley, K. L. *Chem. Comm.* 2008, 3579-3581.
   d. Debbage, P. *Curr. Pharm. Des.* 2009, 15, 153-172.
   e. Chen, J-H.; Ling, R.; Yao, Q.; Wang, L.; Ma, Z.; Li, Y.; Wang, Z.; Xu, H. *World J. Gastroenterol.* 2004, 10, 1989-1991.
   f. Rapoport, N.; Gao, Z.; Kennedy, A. *J. Natl. Cancer Inst.* 2007, 99, 1095-1106.
   g. Steiniger, S. C. J.; Kreuter, J.; Khalansky, A. S.; Skidan, I. N.; Bobruskin, A. I.; Smirnova, Z. S.; Severin, S. E.; Uhl, R.; Kock, M.; Geiger, K. D.; Gelperina, S. E. *Int. J. Cancer.* 2004, 109, 759-767.
   h. Lu, Z.; Yeh, T-K.; Tsai, M.; Au, J. L-S.; Wientjes, M. G. *Clinical Cancer Res.* 2004, 10, 7677-7684.
D. Zhang, Z.; Lee, H. L.; Gan, C. W.; Feng, S-S. *Pharm. Res.* 2008, 25(8), 1925-1935.
E. Zhang, R.; Wang, X.; Wu, C.; Song, M.; Li, J.; Lv, G.; Zhou, J.; Chen, C.; Dai, Y.; Gao, F.; Fu, D.; Li, X.; Guan, Z.; Chen, B. *Nanotechnology* 2006, 17, 3622-3726.
   a. Dong, Y.; Feng, S-S. *Int. J. Pharm.* 2007, 342, 208-214.
   b. Rapoport, N.; Gao, Z.; Kennedy, A. *J. Natl. Cancer Inst.* 2007, 99, 1095-1106.
   c. Li, J.; Wang, X.; Wang, C.; Chen, B.; Dai, Y.; Zhang, R.; Song, M.; Lv, G.; Fu, D. *Chem. Med. Chem.* 2007, 2, 374-378.
   d. Roeske, J. C.; Nunez, L.; Hoggarth, M.; Labay, E.; Weichselbaum, R. R. *Technol. Cancer Res. Treat.* 2007, 6(5), 395-401.
F. O'Neal, D. P.; Hirsch, L. R.; Halas, N. J.; Payne, J. D.; West, J. L. *Cancer Lett.* 2004, 209, 171-176.
   a. El-Sayed, I. H.; Huang, X.; El-Sayed, M. A. *Cancer Lett.* 2005, 239, 129-135.
   b. Kasili, P. M.; Vo-Dinh, T. *NanoBioTechnology* 2005, 1, 245-252.
G. Visaria, R. K.; Griffin, R. J.; Williams, B. W.; Ebbini, E. S.; Paciotti, G. F.; Song, C. W.; Bischof, J. C. *Mol. Cancer Ther.* 2006, 5(4), 1014-1020.

a. Hainfeld, J. F.; Slatkin, D. N.; Smilowitz, H. M. *Phys. Med. Biol.* 2004, 49, N309-N315.
b. Liu, C-J.; Wang, C-H.; Chien, C-C.; Yang, T-Y.; Chen, S-T.; Leng, W-H.; Lee, C-F.; Lee, K-H.; Hwu, Y.; Lee, Y-C.; Cheng, C-L.; Yang, C-S.; Chen, Y. J.; Je, J. H.; Margaritondo, G. *Nanotechnology* 2008, 19, 295104.
c. Kong, T.; Zeng, J.; Wang, X.; Yang, X.; Yang, J.; McQuarrie, S.; McEwan, A.; Roa, W.; Chen, J.; Xing, J. Z. *Small* 2008, 4, 1537-1543.
d. Roeske, J. C.; Nunez, L.; Hoggarth, M.; Labay, E.; Weichselbaum, R. R. *Technology in Cancer Research and Treatment* 2007, 6, 395-401.
H. Wang, S.; Gao, R.; Zhou, F.; Selke, M. *J. Mater. Chem.* 2004, 14, 487-493.
a. Takahashi, J.; Misawa, M. *Nanobiotechnol.* 2007, 3, 116-126.
b. Morgan, N. Y.; Kramer-Marek, G.; Smith, P. D.; Camphausen, K.; Capala, J. *Radiat. Res.* 2009, 171, 236-244.
c. Liu, Y.; Chen, W.; Wang, S.; Joly, A. G. *Appl. Phys. Lett.* 2008, 92, 043901.
d. Liu, Y.; Zhang, Y.; Wang, S.; Pope, C.; Chen, W. *Appl. Phys. Lett.* 2008, 92, 143901.
e. Chatterjee, D. K.; Fong, L. S.; Zhang, Y. *Advanced Drug Delivery Reviews* 2008, 60, 1627-1637.
f. Morgan, N. Y.; Kramer-Marek, G.; Smith, P. D.; Camphausen, K.; Capala, J. *Radiation Research* 2009, 171, 236-244.
g. Takahashi, J.; Misawa, M. *NanoBioTechnology* 2007, 3, 116-126.
I. Henderson, B. W.; Hinger, V. H. *Cancer Res.* 1987, 47, 3110-3114.
a. Brown, J. M.; Giaccia, A. J. *Cancer Res.* 1998, 58, 1408-1416.
b. Hockel, M.; Vaupel, P. *J. Natl. Cancer Inst.* 2001, 93(4), 266-276.
1. Lee, P. C.; Meisel, D. Adsorption and Surface-Enhanced Raman of Dyes on Silver and Gold Sols. *J. Phys. Chem.* 1982, 86, 3391-3395.
2. Jana, N. R.; Gearhart, L.; Murphy, C. J. Wet chemical synthesis of silver nanorods and nanowires of controllable aspect ratio. *Chem. Comm.* 2001, 617-618.
3. Zhu, J-J.; Liao, X-H.; Zhao, X-N.; Chen, H-Y. Preparation of silver nanorods by electrochemical methods. *Materials Letters.* 2001, 49, 91-95.
4. Gu, X.; Nie, C.; Lai, Y.; Lin, C. Synthesis of silver nanorods and nanowires by tartrate-reduced route in aqueous solutions. *Mat. Chem. Phys.* 2006, 96, 217-222.
5. Yang, Y.; Xiong, L.; Shi, J.; Nogami, M. Aligned silver nanorod arrays for surface-enhanced Raman scattering. *Nanotechnology.* 2006, 17, 2670-2674.
6. Jin, R.; Cao, Y.; Mirkin, C. A.; Kelly, K. L.; Schatz, G. C.; Zheng, J. G. Photoinduced Conversion of Silver Nanospheres to Nanoprisms. *Science.* 2001, 294, 1901-1903.
7. Sun, Y.; Xia, Y. Triangular nanoplates of Silver: Synthesis, Characterization, and Use as Sacrificial Templates For Generating Triangular Nanorings of Gold. *Adv. Mater.* 2003, 15(9), 695-699.
8. Lu, L.; Kobayashi, A.; Tawa, K.; Ozaki, Y. Silver Nanoplates with Special Shapes: Controlled Synthesis and Their Surface Plasmon Resonance and Surface-Enhanced Raman Scattering Properties. *Chem. Mater.* 2006, 18(20), 4894-4901.
9. Jiang, X.; Zeng, Q.; Yu, A. A self-seeding coreduction method for shape control of silver nanoplates. *Nanotechnology.* 2006, 17, 4929-4935.
10. Tian, X.; Chen, K.; Cao, G. Seedless, surfactantless photoreduction synthesis of silver nanoplates. *Materials Letters.* 2006, 60, 828-830.
11. Lee, K. Y.; Kim, M.; Kwon, S. K.; Han, S. W. Self-assembled silver nanoprisms monolayers at the liquid/liquid interface. *Materials Letters.* 2006, 60, 1622-1624.
12. Yu, D.; Yam, V. W-W. Controlled Synthesis of Monodisperse Silver Nanocubes in Water. *J. Am. Chem. Soc.* 2004, 126 (41), 13200-13201.
13. Kundu, S.; Maheshwari, V.; Niu, S.; Saraf, R. F. Polyelectrolyte mediated scalable synthesis of highly stable silver nanocubes in less than a minute using microwave irradiation. *Nanotechnology.* 2008, 19, 065604.
14. Nikoobakht, B.; Wang, Z. L.; El-Sayed, M. A. Self-Assembly of Gold Nanorods. *J. Phys. Chem. B.* 2000, 104, 8635-8640.
15. Obare, S. O.; Jana, N. R.; Murphy, C. J. Preparation of Polystyrene- and Silica-Coated Gold Nanorods and Their Use as Templates for the Synthesis of Hollow Nanotubes. *Nano Letters.* 2001, 1(11), 601-603.
16. Jana, N. R.; Gearhart, L.; Murphy, C. J. Wet Chemical Synthesis of High Aspect Ratio Cylindrical Gold Nanorods. *J. Phys. Chem. B.* 2001, 105, 4065-4067.
17. Murphy, C. J.; Jana, N. R. Controlling the aspect ratio of inorganic nanorods and nanowires. *Advanced Materials.* 2002, 14(1), 80-82.
18. Kim, F.; Song, J. H.; Yang, P. Photochemical Synthesis of Gold Nanorods. *J. Am. Chem. Soc.* 2002, 124 (48), 14316-14317.
19. Gao, J.; Bender, C. M.; Murphy, C. J. Dependence of the Gold Nanorod Aspect Ratio on the Nature of the Directing Surfactant in Aqueous Solution. *Langmuir.* 2003, 19, 9065-9070.
20. Busbee, B. D.; Obare, S. O.; Murphy, C. J. An Improved Synthesis of High-Aspect-Ratio Gold Nanorods. *Advanced Materials.* 2003, 15(5), 414-416.
21. Nikoobakht, B.; El-Sayed, M. A. Preparation and Growth Mechanism of Gold Nanorods (NRs) Using Seed-Mediated Growth Method. *Chem. Mater.* 2003, 15, 1957-1962.
22. Gole, A.; Murphy, C. J. Seed-Mediated Synthesis of Gold Nanorods: Role of the Size and Nature of the Seed. *Chem. Mater.* 2004, 16(19), 3633-3640.
23. Gole, A.; Murphy, C. J. Polyelectrolyte-coated Gold Nanorods: Synthesis, Characterization and Immobilization. *Chem. Mater.* 2005, 17(6), 1325-1330.
24. Perez-Juste, J.; Pastoriza-Santos, I.; Liz-Marzan, L. M.; Mulvaney, P. Gold nanorods: Synthesis, characterization and applications. *Coordination Chemistry Reviews.* 2005, 249, 1870-1901.
25. Panarp, P.; Kall, M.; Sutherland, D. S. Optical Properties of Short Range Ordered Arrays of Nanometer Gold Disks Prepared by Colloidal Lithography. *J. Phys. Chem. B.* 2003, 107(24), 5768-5772.
26. Aizpurua, J.; Hanarp, P.; Sutherland, D. S.; Kall, M.; Bryant, G. W.; Garcia de Abajo, F. J. Optical Properties of Gold Nanorings. *Phys. Rev. Lett.* 2003, 90(5), 057401.
27. Genov, D. A.; Sarychev, A. K.; Shalaev, V. M.; Wei, A. Resonant Field Enhancements from Metal Nanoparticle Arrays. *Nano Letters.* 2004, 4(1), 153-158.

28. Shao, Y.; Jin, Y.; Dong, S. Synthesis of gold nanoplates by aspartate reduction of gold chloride. *Chem. Comm.* 2004, 1104-1105.
29. Yamamoto, M.; Kashiwagi, Y.; Sakata, T.; Mori, H.; Nakamoto, M. Synthesis and Morphology of Star-Shaped Gold Nanoplates Protected by Poly(N-vinyl-2-pyrrolidone). *Chem. Mater.* 2005, 17(22), 5391-5393.
30. Sun, X.; Dong, S.; Wang, E. High-Yield Synthesis of Large Single-Crystalline Gold Nanoplates through a Polyamine Process. *Langmuir.* 2005, 21(10), 4710-4712.
31. Millstone, J. E.; Metraux, G. S.; Mirkin, C. A. Controlling the Edge Length of Gold Nanoprisms via a Seed-Mediated Approach. *Adv. Functional Mat.* 2006, 16, 1209-1214.
32. Huang, W.; El-Sayed, M. A. Pulsed laser photothermal annealing and ablation of plasmonic nanoparticles. *European Physical Journal Special Topics.* 2008, 153, (223-230).
33. Millstone, J. E.; Georganopoulou, D. G.; Xu, X.; Wei, W.; Li, S.; Mirkin, C. A. DNA-Gold Triangular Nanoprism Conjugates. *Small.* 2008, 4(12), 2176-2180.
34. Huang, C-J.; Wang, Y-H.; Chiu, P-H.; Shih, M-C.; Meen, T-H. Electrochemical synthesis of gold nanocubes. *Materials Letters.* 2006, 60, 1896-1900.
35. Kundu, S.; Panigrahi, S.; Praharaj, S.; Basu, S.; Ghosh, S. K.; Pal, A.; Pal, T. Anisotropic growth of gold clusters to gold nanocubes under UV irradiation. *Nanotechnology.* 2007, 18, 075712.
36. Kumar, P. S.; Pastoriza-Santos, I.; Rodriguez-Gonzalez, B.; Garcia de Abajo, F. J.; Liz-Marzan, L. M. High-yield synthesis and optical response of gold nanostars. *Nanotechnology.* 2008, 19, 015606.
37. Nehl, C. L.; Liao, H.; Hafner, J. H. Plasmon resonant molecular sensing with single gold nanostars. *Proc. SPIE.* 2006, 6323, 63230G.
38. Khoury, C. G.; Vo-Dinh, T. Gold Nanostars For Surface-Enhanced Raman Scattering: Synthesis, Characterization and Optimization. *J. Phys. Chem. C.* 2008, 112(48), 18849-18859.
39. Thiel, A. J.; Frutos, A. G.; Jordan, C. E.; Corn, R. M.; Smith, L. M. In Situ Surface Plasmon Resonance Imaging Detection of DNA Hybridization to Oligonucleotide Arrays on Gold Surfaces. *Anal. Chem.* 1997, 69, 4948-4956.
40. Storhoff, J. J.; Elghanian, R.; Mucic, R. C.; Mirkin, C. A.; Letsinger, R. L. One-Pot Colorimetric Differentiation of Polynucleotides with Single Base Imperfections Using Gold Nanoparticle Probes. *J. Am. Chem. Soc.* 1998, 120, 1959-1964.
41. Isola, N. R.; Stokes, D. L.; Vo-Dinh, T. Surface enhanced Raman gene probe for HIV detection. *Anal. Chem.* 1998, 70, 1352-1356.
42. Allain, L. R.; Vo-Dinh, T. Surface-enhanced Raman scattering detection of the breast cancer susceptibility gene BRCA1 using a silver-coated microarray platform. *Anal. Chim. Acta.* 2002, 469, 149-154.
43. Vo-Dinh T. Nano-biosensors: Probing the sanctuary of individual living cells. *J. Cellular Biochem, Suppl.* 2002, 39, 154.
44. Culha, M.; Stokes, D.; Allain, L. R.; Vo-Dinh, T. Surface-enhanced Raman scattering (SERS) Substrate Based on Self-assembled Monolayer (SAM) for Use in Gene Diagnostics. *Anal. Chem.* 2003, 75, 6196-6201.
45. Hutter, E.; Pileni, M-P. Detection of DNA Hybridization by Gold Nanoparticle Enhanced Transmission Surface Plasmon Resonance Spectroscopy. *J. Phys. Chem. B.* 2003, 107(27), 6497-6499.
46. Chen, S-J.; Chien, F. C.; Lin, G. Y.; Lee, K. C. Enhancement of the resolution of surface plasmon resonance biosensors by control of the size and distribution of nanoparticles. *Optics Letters.* 2004, 29(12), 1390-1392.
47. Wabuyele, M. B.; Vo-Dinh, T. Detection of human immunodeficiency virus type 1 DNA sequence using plasmonics nanoprobes. *Anal. Chem.* 2005, 77, 7810-7815.
48. Wang, H-S.; Vo-Dinh, T. Multiplex detection of breast cancer biomarkers using plasmonic molecular sentinel nanoprobes. *Nanotechnology.* 2009, 6, 627-638.
49. Nam, J-M.; Thaxton, C. S.; Mirkin, C. A. Nanoparticle-Based Bio-Bar Codes for the Ultrasensitive Detection of Proteins. *Science.* 2003, 26, 301(5641), 1884-1886.
50. Cognet, L.; Tardin, C.; Boyer, D.; Choquet, D.; Tamarat, P.; Lounis, B. Single metallic nanoparticle imaging for protein detection in cells. *Proc. Natl. Acad. Sci.* 2003, 100(20), 11350-11355.
51. Green, R. J.; Davies, J.; Davies, M. C.; Roberts, C. J.; Tendler, S. J. B. Surface plasmon resonance for real time in situ analysis of protein adsorption to polymer surfaces. *Biomaterials.* 1997, 18(5), 405-413.
52. Homola, J.; Yee, S. S.; Gauglitz, G. Surface plasmon resonance sensors: review. *Sensors and Actuators B: Chemical.* 1999, 54(1-2), 3-15.
53. Homola, J. Present and future of surface plasmon resonance biosensors. *Analytical and Bioanalytical Chemistry.* 2003, 377(3), 528-539.
54. Karlsson, R. SPR for molecular interaction analysis: a revew of emerging application areas. *J. Molecular Recognition.* 2004, 17(3), 151-161.
55. Taton, T. A.; Mirkin, C. A.; Letsinger, R. L. Scanometric DNA Array Detection with Nanoparticle Probes. *Science.* 2000, 289(5485), 1757-1760.
56. Schmidt, H.; Jonschker, G.; Goedicke, S.; Mennig, M. The Sol-Gel Process as a Basic Technology for Nanoparticle-Dispersed Inorganic-Organic Composites. *J. Sol-Gel Science and Technology.* 2000, 19, 39-51.
57. Santra, S.; Zhang, P.; Wang, K.; Tapec, R.; Tan, W. Conjugation of Biomolecules with Luminophore-Doped Silica Nanoparticles for Photostable Biomarkers. *Anal. Chem.* 2001, 73, 4988-4993.
58. Santra, S.; Wang, K.; Tapec, R.; Tan, W. Development of novel dye-doped silica nanoparticles for biomarker application. *J. Biomedical Optics.* 2001, 6(2), 160-166.
59. Ye, Z.; Tan, M.; Wang, G.; Yuan, J. Novel fluorescent europium chelate-doped silica nanoparticles: preparation, characterization and time-resolved fluorometric application. *J. Materials Chemistry.* 2004, 14, 851-856.
60. Lian, W.; Litherland, S. A.; Badrane, H.; Tan, W.; Wu, D.; Baker, H. V.; Gulig, P. A.; Lim, D. V.; Jin, S. Ultrasensitive detection of biomolecules with fluorescent dye-doped nanoparticles. *Analytical Biochemistry.* 2004, 334, 135-144.
61. Santra, S.; Liesenfeld, B.; Bertolino, C.; Dutta, D.; Cao, Z.; Tan, W.; Moudgil, B. M.; Mericle, R. A. Fluorescence lifetime measurements to determine the core-shell nanostructure of FITC-doped silica nanoparticles: An optical approach to evaluate nanoparticle photostability. *J. Luminescence.* 2006, 117, 75-82.
62. Wang, Y.; Qin, W.; Zhang, J.; Cao, C.; Zhang, J.; Jin, Y.; Ren, X.; Zheng, Z.; Lu, S. Synthesis, photoluminescence and bioconjugation of rare-earth (Eu) complexes-embedded silica nanoparticles. *Solid State Communications.* 2007, 142, 689-693.
63. Choi, J.; Burns, A. A.; Williams, R. M.; Zhou, Z.; Flesken-Nikitin, A.; Zipfel, W. R.; Wiesner, U.; Nikitin, A. Y. Core-shell silica nanoparticles as fluorescent labels for nanomedicine. *J. Biomedical Optics.* 2007, 12(6), 064007.
64. Xu, Y.; Li, Q.n Multiple Fluorescent Labeling of Silica Nanoparticles with Lanthanide Chelates for Highly Sensitive Time-Resolved Immunofluorometric Assays. *Clinical Chemistry.* 2007, 53(8), 1503-1510.
65. SiO2 functionalized with proteins. (65 and refs therein).
66. Medintz, I. L.; Clapp, A. R.; Mattoussi, H.; Goldman, E. R.; Fisher, B.; Mauro, J. M. Self-assembled nanoscale biosensors based on quantum dot FRET donors. *Nature Materials.* 2003, 2, 630-638.
67. Ji, Z X.; Zzheng, J.; Xu, J.; Rastogi, V. K.; Cheng, T-C.; DeFrank, J. J.; Leblanc, R. M. (CdSe)ZnS Quantum Dots and Organophosphorase Hydrolase Bioconjugate as Biosensors for Detection of Paraoxon. *J. Phys. Chem. B.* 2005, 109(9), 3793-3799.
68. Yeh, H.; Ho, Y.; Wang, T. Quantum dot-mediated biosensing assays for specific nucleic acid detection. *Nanomedicine: Nanotechnology, Biology and Medicine.* 2005, 1(2), 115-121.
69. Nadeau, J. L.; Clarke, S. J.; Hollman, C. A.; Bahcheli, D. M.; Khatchadourian, R. A.; Bachir, A.; Wiseman, P. Quantum dot systems for specific biosensing applications. *Colloidal Quantum Dots for Biomedical Applications II.* Osinski, M.; Jovin, T. M.; Yamamoto, K. (eds). *Proc. SPIE.* 2007, 6448, 64480M.
70. Selvan, S. T.; Tan, T. T.; Ying, J. Y. Robust, Non-Cytotoxic, Silica-Coated CdSe Quantum Dots with Efficient Photoluminescence. *Adv. Mater.* 2005, 17(13), 1620-1625.
71. Cao, Y-C.; Huang, Z-L.; Liu, T-C.; Wang, H-Q.; Zhu, X-X.; Zhao, Y-D. Preparation of silica encapsulated quantum dot encoded beads for multiplex assay and its properties. *Analytical Biochemistry.* 2006, 351(2), 193-200.
72. Wang, Y.; Niu, S-H.; Zhang, Z-J.; Wang, H-T.; Yuan, C-W.; Fu, D-G. Silica Coating of Water-Soluble CdTe/CdS Core-Shell Nanocrystals by Microemulsion Method. *Chinese Journal of Chemical Physics.* 2007, 20(6), 685-689.
73. Yang, Y.; Jing, L.; Yu, X.; Yan, D.; Gao, M. Coating Aqueous Quantum Dots with Silica via Reverse Microemulsion Method: Toward Size-Controllable and Robust Fluorescent Nanoparticles. *Chem Mater.* 2007, 19(17), 4123-4128.
74. Tan, T. T.; Selvan, S. T.; Zhao, L.; Gao, S.; Ying, J. Y. Size Control, Shape Evolution and Silica Coating of Near-Infrared-Emitting PbSe Quantum Dots. *Chem. Mater.* 2007, 19(13), 3112-3117.
75. Zhou, X.; Wang, X.; Liu, F.; Chen, Z.; Kasuya, A. Luminescence Stability of the Silica Encapsulated CdSe Quantum Dots. *Current Nanoscience.* 2008, 4(1), 88-91.
76. Santra, S.; Tapec, R.; Theodoropoulou, N.; Dobson, J.; Hebard, A.; Tan, W. Synthesis and Characterization of Silica-Coated Iron Oxide Nanoparticles in Microemulsion: The Effect of Nonionic Surfactants. *Langmuir.* 2001, 17(10), 2900-2906.
77. Zhang, C.; Wangler, B.; Morgenstern, B.; Zentgraf, H.; Eisenhut, M.; Untenecker, H.; Kruger, R.; Huss, R.; Seliger, C.; Semmler, W.; Kiessling, F. Silica- and Alkoxysilane-Coated Ultrasmall Superparamagnetic Iron Oxide Particles: A Promising Tool To Label Cells for Magnetic Resonance Imaging. *Langmuir.* 2007, 23(3), 1427-1434.
78. Ren, C.; Li, J.; Liu, Q, Ren, J.; Chen, X.; Hu, Z.; Xue, D. Synthesis of Organic Dye-Impregnated Silica Shell-Coated Iron Oxide Nanoparticles by a New Method. *Nanoscale Research Letters.* 2008, 3(12), 496-501.
79. Liu, S.; Zhang, Z.; Wang, Y.; Wang, F.; Han, M-Y. Surface-functionalized silica-coated gold nanoparticles and their bioapplications. *Talanta.* 2005, 67(3), 456-461.
80. Kobayashi, Y.; Katakami, H.; Mine, E.; Nagao, D.; Konno, M.; Liz-Marzan, L. M. Silica coating of silver nanoparticles using a modified Stober method. *Journal of Colloid and Interface Science.* 2005, 283(2), 392-396.
81. Liu, S.; Zhang, Z.; Han, M. Gram-Scale Synthesis and Biofunctionalization of Silica-Coated Silver Nanoparticles for Fast Colorimetric DNA Detection. *Anal. Chem.* 2005, 77(8), 2595-2600.
82. Xue, C.; Chen, X.; Hurst, S. J.; Mirkin, C. A. Self-Assembled Monolayer Mediated Silica Coating of Silver Triangular Nanoprisms. *Advanced Materials.* 2007, 19(22), 4071-4074.
83. Wang, H.; Shaefer, K.; Moeller, M. In situ Immobilization of Gold Nanoparticle Dimers in Silica Nanoshell by Microemulsion Coalescence. *J. Phys. Chem. C.* 2008, 112(9), 3175-3178.
84. Kanehara, M.; Watanabe, Y.; Toshiharu, T. Thermally Stable Silica-Coated Hydrophobic Gold Nanoparticles. *Journal of Nanoscience and Nanotechnology.* 2009, 9(1), 673-675.
85. Kerker, M. Electromagnetic model for surface-enhanced Raman-scattering (SERS) on metal colloids. *Acc. Chem. Res.* 1984, 17, 271-277.
86. Oldenburg, S.; Averitt, R. D.; Westcott, S.; Halas, N. J. Nanoengineering of Optical Resonances. *Chem. Phys. Lett.* 1998, 288, 243-247.
87. Averitt, R. D.; Westcott, S. L.; Halas, N. J. The Linear Optical Properties of Gold Nanoshells. *J. Opt. Soc. Am.* 1999, 16, 1824-1832.
88. Oldenburg, S. J.; Jackson, J. B.; Westcott, S. L.; Halas, N. J. Infrared Extinction Properties of Gold Nanoshells. *Appl. Phys. Lett.* 1999, 75, 2897-2899.
89. Oldenburg, S. J.; Westcott, S. L.; Averitt, R. D.; Halas, N. J. Surface enhanced Raman scattering in the near infrared using metal nanoshell substrates. *J. Chem. Phys.* 1999, 111, 4729-4735.
90. Jackson, J. B.; Halas, N. J. Surface-enhanced Raman scattering on tunable plasmonic nanoparticle substrates. *Proc. Natl. Acad. Sci. USA.* 2004, 101, 17930-17935.
91. Jain, P. K.; Lee, K. S.; El-Sayed, I. H.; El-Sayed, M. A. Calculated Absorption and Scattering Properties of Gold Nanoparticles of Different Size, Shape and Composition: Applications in Biological Imaging and Biomedicine. *J. Phys. Chem. B.* 2006, 110, 7238-7248.
92. Norton, S. J.; Vo-Dinh, T. Plasmon Resonances of Nanoshells of Spheroidal Shape. *IEEE Trans. Nanotechnology.* 2007, 6(6), 627-638.
93. Norton, S. J.; Vo-Dinh, T. Spectral bounds on plasmon resonances for Ag and Au prolate and oblate nanospheroids. *J. Nanophotonics.* 2008, 2, 029501.

94. Pal, A.; Pal, T.; Stokes, D. L.; Vo-Dinh, T. Photochemically prepared gold nanoparticles: A substrate for surface-enhanced Raman scattering. *Current Science.* 2003, 84, 1342-1346.
95. Pal, A.; Stokes, D. L.; Vo-Dinh, T. Photochemically Prepared Gold Metal film in a Carbohydrate-based Polymer: a Practical Solid substrate for Surface-enhanced Raman Scattering. *Current Science.* 2004, 87, 486-491.
96. Martin, I. R.; Goutadier, C.; Guy, S.; Guyot, Y.; Boulon, G.; Cohen-Adad, M-T.; Joubert, M-F. Room temperature photon avalanche upconversion in Tm3+: Y2O3 crystals. *Phys. Rev. B.* 1999, 60, 7252-7257.
97. Chen, G. Y.; Somesfalean, G.; Zhang, Z. G.; Sun, Q.; Wang, F. P. Ultraviolet upconversion fluorescence in rare-earth-ion-doped Y2O3 induced by infrared diode laser excitation. *Optics Letters.* 2007, 32(1), 87-89.
98. Yang, X.; Xiao, S.; Liu, Z.; Yan, X. H. Sensitizer-dependent up-conversion of Ho3+ in nanocrystalline Y2O3. *Applied Physics B.* 2007, 86(1), 77-82.
99. Anh, T-K.; Benalloul, P.; Barthou, C.; Giang, L T-K.; Vu, N.; Minh, L-Q. Luminescence, Energy Transfer, and Upconversion Mechanisms of Y2O3 Nanomaterials Doped with Eu3+, Tb3+, Tm3+, Er3+ and Yb3+ Ions. *Journal of Nanomaterials.* 2007, 2007, 48247.
100. Lu, Q.; Li, A-H.; Guo, F-Y.; Sun, L.; Zhao, L-C. The two-photon excitation of SiO2-coated Y2O3: Eu3+ nanoparticles by a near-infrared femtosecond laser. *Nanotechnology.* 2008, 19(20), 205704.
101. Lu, Q.; Li, A-H.; Guo, F-Y.; Sun, L.; Zhao, L-C. Experimental study on the surface modification of Y2O3:Tm3+/Yb3+ nanoparticles to enhance upconversion fluorescence and weaken aggregation. *Nanotechnology.* 2008, 19(14), 145701.
102. Luo, J-M.; Li, Y-X.; Deng, L-P.; Yuan, Y-R.; Chen, W-F. Fabrication and Up-Conversion Luminescence of Er3+:Y2O3 Nanoparticles. *Journal of Nanoscience and Nanotechnology.* 2008, 8(3), 1121-1213.
103. Li, Y.; Zhang, Y.; Hong, G.; Yu, Y. Upconversion luminescence of Y2O3:Er3+,Yb3+ nanoparticles prepared by a homogenous precipitation method. *Journal of Rare Earths.* 2008, 26(3), 450-454.
104. Liang, H.; Chen, G.; Liu, H.; Zhang, Z. Ultraviolet upconversion luminescence enhancement in Yb3+/Er3+-codoped Y2O3 nanocrystals induced by tridoping with Li+ ions. *Journal of Luminescence.* 2009, 129(3), 197-202.
105. Williams, D. K.; Bihari, B.; Tissue, B. M.; McHale, J. M. Preparation and Fluorescence Spectroscopy of Bulk Monoclinic Eu3+:Y2O3 and Comparison to Eu3+:Y2O3 Nanocrystals. *J. Phys. Chem. B.* 1998, 102(6), 916-920.
106. Meltzer, R. S.; Feofilov, S. P.; Tissue, B.; Yuan, H. B. Dependence of fluorescence lifetimes of Y2O3:Eu3+ nanoparticles on the surrounding medium. *Phys. Rev. B.* 1999, 60, R14012-R14015.
107. Lian, J.; Yang, L.; Chen, X. Y.; Liu, G. K.; Wang, L. M.; Ewing, R. C.; Shi, D. Deposition of ultrathin rare-earth doped Y2O3 phosphor films on alumina nanoparticles. *Nanotechnology.* 2006, 1351-1354.
108. Wu, Y. C.; Garapon, C.; Bazzi, R.; Pillonnet, A.; Tillement, O.; Mugnier, J. Optical and fluorescent properties of Y2O3 sol gel planar waveguides containing Tb3+ doped nanocrystals. *Applied Physics A.* 2007, 87(4), 697-704.
109. Tkachenko, A. G.; Xie, H.; Coleman, D.; Glomm, W.; Ryan, J.; Anderson, M. F.; Franzen, S.; Feldheim, D. L. Multifunctional Gold Nanoparticle-Peptide Complexes for Nuclear Targeting. *J. Am. Chem. Soc.* 2003, 125, 4700-4701.
110. Tkachenko, A. G.; Xie, H.; Liu, Y.; Coleman, D.; Ryan, J.; Glomm, W. R.; Shipton, M. K.; Franzen, S.; Feldheim, D. L. Cellular Trajectories of Peptide-Modified Gold Particle Complexes: Comparison of Nuclear Localization Signals and Peptide Transduction Domains. *Bioconjugate Chem.* 2004, 15, 482-490.
111. Koch, A. M.; Reynolds, F.; Merkle, H. P.; Weissleder, R.; Josephson, L. Transport of Surface-Modified Nanoparticles Through Cell Monolayers. *ChemBioChem.* 2005, 6, 337-345.
112. Berry, C. C. Intracellular delivery of nanoparticles via the HIV-1 tat peptide. *Nanomedicine.* 2008, 3(3), 357-365.
113. Selphati, O.; Szoka, F. C. Jr. Intracellular distribution and mechanism of delivery of oligonucleotides mediated by cationic lipids. *Pharm. Res.* 1996, 13, 1367-1372.
114. Suh, J.; Wirtz, D.; Hanes, J. Efficient active transport of gene nanocarriers to the cell nucleus. *Proc. Natl. Acad. Sci. USA.* 2003, 100, 3878-3882.
115. Park, Y. J.; Liang, J. F.; Ko, K. S.; Kim, S. W.; Yang, V. C. Low molecular weight protamine as an efficient and nontoxic gene carrier. *J. Gene. Med.* 2003, 5, 700-711.
116. Gait, M. J. Peptide-mediated cellular delivery of antisense oligonucleotides and their analogues. *Cell. Mol. Life. Sci.* 2003, 60, 844-853.
117. Labhasetwar, V. Nanotechnology for drug and gene therapy: the importance of understanding molecular mechanisms of delivery. *Curr. Opin. Biotechnol.* 2005, 16, 674-680.
118. Kida, S.; Maeda, M.; Hojo, K.; Eto, Y.; Gao, J-Q.; Kurachi, S.; Mizuguchi, H.; Hayakawa, T.; Mayumi, T.; Nakagawa, S.; Kawasaki, K. Design and synthesis of a Tat-related gene transporter: A tool for carrying the adenovirus vector into cells. *Bioorganic and Medicinal Chemistry Letters.* 2006, 16, 743-745.
119. Santra, S.; Yang, H.; Dutta, D.; Stanley, J. T.; Holloway, P. H.; Tan, W.; Moudgil, B. M.; Mericle, R. A. TAT conjugated, FITC doped silica nanoparticles for bioimaging applications. *Chem. Commun.* 2004, 2810-2811.
120. Santra, S.; Yang, H.; Stanley, J. T.; Holloway, P. H.; Moudgil, B. M.; Walter, G.; Mericle, R. A. Rapid and effective labeling of brain tissue using TAT-conjugated CdS:Mn/ZnS quantum dots. *Chem. Commun.* 2005, 3144-3146.
121. Delehanty, J. B.; Medintz, I. L.; Pons, T.; Brunel, F. M.; Dawson, P. E.; Mattoussi, H. Self-Assembled Quantum Dot-Peptide Bioconjugates for Selective Intracellular Delivery. *Bioconjugate Chem.* 2006, 17, 920-927.
122. Zhou, M.; Ghosh, I. Quantum Dots and Peptides: A Bright Future Together. *Peptide Science.* 2006, 88(3), 325-339.
123. Hasegawa, S.; Hirashima, N.; Nakanishi, M. Microtubule involvement in the intracellular dynamics for gene transfection mediated by cationic liposomes. *Gene. Ther.* 2001, 8, 1669-1673.
124. Fretz, M. M.; Koning, G. A.; Mastrobattista, E.; Jiskoot, W.; Storm, G. OVCAR-3 cells internalize TAT-peptide modified liposomes by endocytosis. *Biochimica et Biophysica Acta.* 2004, 48-56.

125. Fawell, S.; Seery, J.; Daikh, Y.; Moore, C.; Chen, L. L.; Pepinsky, B.; Barsoum, J. Tat-mediated delivery of heterologous proteins into cells. *Proc. Natl. Acad. Sci. USA.* 1994, 91(2), 664-668.

126. Dietz, G. P. H.; Bahr, M. Peptide-enhanced cellular internalization of proteins in neuroscience. *Brain Reseearch Bulletin.* 2005, 68, 103-114.

127. Torchilin, V. P.; Levchenko, T. S.; Rammohan, R.; Volodina, N.; Papahadjopoulos-Sternberg, B.; D'Souza, G. G. M. Cell transfection in vitro and in vivo with nontoxic TAT peptide-liposome-DNA complexes. *Proc. Natl. Acad. Sci. USA.* 2003, 100(4), 1972-1977.

128. Manickam, D. S.; Bisht, H. S.; Wan, L.; Mao, G.; Oupicky, D. Influence of TAT-peptide polymerization on properties and transfection activity of TAT/DNA polyplexes. *Journal of Controlled Release.* 2004, 102(1), 293-306.

129. Kim, K.; Han, J. S.; Kim, H. A.; Lee, M. Expression, purification and characterization of TAT-high mobility group box-1A peptide as a carrier of nucleic acids. *Biotechnology Letters.* 2008, 30(8), 1331-1337.

130. Malik, M. A.; O'Brien, P. Revaprasadu, N. A Simple Route to the Synthesis of Core/Shell Nanoparticles of Chalcogenides. *Chem. Mater.* 2002, 14(5), 2004-2010.

131. Zhang, L.; Xia, D.; Xhen, Q. Nanoparticles and TiO2 Nanobubbles. *J. Nanoparticle Research.* 2006, 8(1), 23-28.

132. Chen, F.; Gao, Q.; Hong, G.; Ni, J. Synthesis of magnetite core shell nanoparticles by surface-initiated ring-opening polymerization of L-lactide. *J. Magnetisim & Magnetic Materials.* 2008, 320(13), 1921-1927.

133. Yonezawa, T.; Sutoh, M.; Kunitake, T. Practical Preparation of Size-Controlled Gold Nanoparticles in Water. *Chemistry Letters.* 1997, 619-620.

134. Link, S.; Wang, Zz. L.; El-Sayed, M. A. Alloy Formation of Gold-Silver Nanoparticles and the Dependence of the Plasmon Absorption on Their Composition. *J Phys. Chem. B.* 1999, 103, 3529-3533.

135. Link, S.; El-Sayed, M. A. Size and Temperature Dependence of the Plasmon Absorption of Colloidal Gold Nanoparticles. *J. Phys. Chem. B.* 1999, 103, 4212-4217.

136. Westcott, S. L.; Oldenburg, S. J.; Lee, T. R.; Halas, N. J. Construction of simple gold nanoparticle aggregates with controlled plasmon-plasmon interactions. *Chem. Phys. Lett.* 1999, 300, 651-655.

137. Dulkeith, E.; Morteani, A. C.; Niedereichholz, T.; Klar, T. A.; Feldmann, J.; Levi, S. A.; van Veggel, F. C. J. M.; Reinhoudt, D. N., Moller, M.; Gittins, D. I. Fluorescence Quenching of Dye Molecules near Gold Nanoparticles: Radiative and Nonradiative Effects. *Phys. Rev. Lett.* 2002, 89(20), 203002.

138. Orendorff, C. J.; Sau, T. K.; Murphy, C. J. Shape-Dependent Plasmon-Resonant Gold Nanoparticles. *Small.* 2006, 2(5), 636-639.

139. Hu, J.; Wang, Z.; Li, J. Gold Nanoparticles With Special Shapes: Controlled Synthesis, Surface-enhanced Raman Scattering, and the Application in Biodetection. *Sensors.* 2007, 7, 3299-3311.

140. Di Felice, R.; Selloni, A. Adsorption modes of cysteine on Au(111): Thiolate, amino-thiolate, disulfide. *J. Chem. Phys.* 2004, 120(10), 4906-4914.

141. Varghese, N.; Vivekchand, S. R. C.; Govindaraj, A.; Rao, C. N. R. A calorimetric investigation of the assembly of gold nanorods to form necklaces. *Chem. Phys. Lett.* 2008, 450, 340-344.

142. Scaffidi, J. P.; Gregas, M. K.; Seewaldt, V.; Vo-Dinh, T. SERS-based plasmonic nanobiosensing in single living cells. *Analytical and Bioanalytical Chemistry.* 2009, 393(4), 1135-1141.

143. Vo-Dinh, T.; Yan, F.; Wabuyele, M. B. Surface-Enhanced Raman Scattering for Biomedical Diagnostics and Molecular Imaging. *Topics in Applied Biophysics.* 2006, 103, 409-426.

144. Wang, H-N.; Vo-Dinh, T. Multiplex detection of breast cancer biomarkers using plasmonic molecular sentinel nanoprobes. *Nanotechnology.* 2009, 20, 065101.

145. Vo-Dinh, T.; Yan, F.; Wabuyele, M. B. Surface-enhanced Raman scattering for medical diagnostics and biological imaging. *J. Raman Spectroscopy.* 2005, 36(6-7), 640-647.

146. Wabuyele, M. B.; Yan, F.; Griffin, G. D.; Vo-Dinh, T. Hyperspectral surface-enhanced Raman imaging of labeled silver nanoparticles in single cells. *Rev. Sci. Instruments.* 2005, 76, 063710.

147. Gregas, M. K.; Yan, F.; Scaffidi, J.; Wang, H-S.; Khoury, C.; Zhang, Y.; Vo-Dinh, T. Tracking SERS-active nanoprobe intracellular uptake for chemical and biological sensing. *Proc. SPIE.* 2007, 6755, 67550H.

148. Demers, L. M.; Mirkin, C. A.; Mucic, R. C.; Reynolds, R. A. III.; Letsinger, R. L.; Elghanian, R.; Viswanadham, G. A Fluorescence-Based Method for Determining the Surface Coverage and Hybridization Efficiency of Thiol-Capped Oligonucleotides Bound to Gold Thin Films and Nanoparticles. *Anal. Chem.* 2000, 72, 5535-5541.

149. Huang, E.; Satjapipat, M.; Han, S.; Zhou, F. Surface Structure and Coverage of an Oligonucleotide Probe Tethered onto a Gold Substrate and Its Hybridization Efficiency for a Polynucleotide Target. *Langmuir.* 2001, 17(4), 1215-1224.

150. Pal, S.; Kim, M. J.; Song, J. M. Quantitation of surface coverage of oligonucleotides bound to chip surfaces: a fluorescence-based approach using alkaline phosphatase digestion. *Lab on a Chip.* 2008, 8, 1332-1341.

151. Hill, H. D.; Millstone, J. E.; Banholzer, M. J.; Mirkin, C. A. The Role Radius of Curvature Plays in Thiolated Oligonucleotide Loading on Gold Nanoparticles. *ACS Nano.* 2009, 3(2), 418-424.

J. Taxak, V. B.; Khatkar, S. P.; Han, S-D.; Kumar, R.; Kumar, M. *J. Alloys Compounds* 2009, 469, 224-228.

a. Hartl, W.; Beck, Ch.; Roth, M.; Meyer, F.; Hempelmann, R. *Ber. Bunsenges. Phys. Chem.* 1997, 11, 1714-1717.

b. Zako, T.; Nagata, H.; Terada, N.; Sakono, M.; Soga, K.; Maeda, M. *J. Mater. Sci.* 2008, 43, 5325-5330.

c. Kaczmarek, W. A.; Riesen, H. *J. Mater. Sci.* 2006, 41, 8320-8328.

d. Nelson, J. A.; Wagner, M. J. *Chem. Mater.* 2002, 14, 915-917.

e. Hirai, T.; Kawamura, Y.; Komasawa, I. *Journal of Colloid and Interface Science* 2004, 275, 508-513.

f. Vetrone, F.; Boyer, J-C.; Capobianco, J. A.; Speghini, A.; Bettinelli, M. *Nanotechnology* 2004, 15, 75-81.

g. Gordon, W. O.; Tissue, B. M.; Morris, J. R. *J. Phys. Chem. C* 2007, 111, 3233-3240.

h. Chen, W.; Zhang, J.; Westcott, S. L.; Joly, A. G.; Malm, J-O.; Bovin, J-O. *J. Appl. Phys.* 2006, 99, 034302.

i. Lian, H.; Zhang, M.; Liu, J.; Ye, Z.; Yan, J.; Shi, C. *Chem. Phys. Lett.* 2004, 395, 362-365.

J. Liu, Y.; Chen, W.; Wang, S.; Joly, A. G.; Westcott, S.; Woo, B. K. *J. Appl. Phys.* 2008, 103, 063105.
k. Klaasen, N. V.; Kedrov, V. V.; Kurlov, V. N.; Ossipyan, Y. A.; Shmurak, S. Z.; Shmyt'ko, I. M.; Strukova, G. K.; Kobelev, N. P.; Kudrenko, E. A.; Krivko, O. A.; Kiselev, A. P.; Bazhenov, A. V.; Fursova, T. N. *IEEE Trans. Nucl. Sci.* 2008, 55, 1536-1541.
l. Geng, J.; Zhang, J-R.; Hong, J-M.; Zhu, J-J. *International Journal of Modern Physics B* 2005, 19, 2734-2739.
m. Zhang, H.; Lu, M.; Xiu, Z.; Zhou, G.; Wang, S.; Zhou, Y.; Wang, S. *Materials Science and Engineering B* 2006, 130, 151-157.
n. Cicillini, S. A.; Pires, A. M.; Serra, O. A. *J. Alloys Compounds* 2004, 374, 169-172.
o. Guo, F.; Li, H.; Zhang, Z.; Meng, S.; Li, D. *Materials Research Bulletin* 2009, 44, 1565-1568.
p. Lv, Y.; Wu, X.; Wu, D.; Huo, D.; Zhao, S. *Powder Technology* 2007, 173, 174-178.
q. Fadlalla, H. M. H.; Tang, C. C. *Optical Materials* 2008, 31, 401-404.
r. Brown, S. S.; Im, H-J.; Rondinone, A. J.; Dai, S. *Journal of Colloid and Interface Science* 2005, 292, 127-132.
s. Ledoux, G.; Mercier, B.; Louis, C.; Dujardin, C.; Tillement, O.; Perriat, P. *Radiation Measurements* 2004, 38, 763-766.
t. Montes, P. J. R.; Valerio, M. E. G.; Azevedo, G. de M. *Nuclear Instruments and Methods in Physics Research B* 2008, 266, 2923-2927.
K. Sveier, H.; Kvamme, B. O.; Raae, A. J. *Aquaculture Nutrition* 2001, 20017, 255-264.
a. Reis, P. A.; Valente, L. M. P.; Almeida, C. M. R. *Food Chemistry* 2008, 108, 1094-1098.
b. Schubert, D.; Dargusch, R.; Raitano, J.; Chan, S-W. *Biochemical and Biophysical Research Communications* 2006, 342, 86-91.
L. Torchilin, V. P.; Levchenko, T. S.; Rammohan, R.; Volodina, N.; Papahadjopoulos-Sternberg, B.; D'Souza, G. G. M. *Proc. Natl. Acad. Sci. USA.* 2003, 100(4), 1972-1977.
a. Manickam, D. S.; Bisht, H. S.; Wan, L.; Mao, G.; Oupicky, D. *Journal of Controlled Release.* 2004, 102(1), 293-306.
b. Kim, K.; Han, J. S.; Kim, H. A.; Lee, M. *Biotechnology Letters.* 2008, 30(8), 1331-1337.
M. Traina, C. A.; Schwartz, J. *Langmuir* 2007, 23, 9158-9161.
Traina, C. A.; Dennes, T. J.; Schwartz, J. *Bioconjugate Chem.* 2009, 20, 437-439.
S. See K, K(a).
T. Weisenthal, L. M.; Dill, P. L.; Kurnick, N. B.; Lippman, M. E. *Cancer Res.* 1983, 43, 258-264.
a. Berridge, M. V.; Tan, A. S.; McCoy, K. D.; Wang, R. *Biochemica* 1996, 4, 14-19.
b. Mueller, H.; Kassack, M. U.; Wiese, M. *J Biomol. Screen.* 2004, 9, 506-515. (also U1)
c. Schubert, D., Dargusch, R., Raitano, J., Chain, S-W. *Biochem. Biophys. Res. Comm.* 2006, 342, 86-91.

The invention claimed is:

1. A functionalized nanoparticle, consisting of:
a core, having a shell on at least a portion thereof, wherein the core is a material that can convert applied X-ray energy into emitted UV energy and wherein the shell is a plasmonics active material selected from the group consisting of gold, silver, gallium, platinum, palladium, nickel, aluminum and metal alloys consisting of a combination of the above materials, wherein the material that can convert applied X-ray energy into emitted UV energy is a material selected from the group consisting of metals, quantum dots, semiconductor materials, scintillation and phosphor materials, materials that exhibit X-ray excited luminescence (XEOL), organic solids, metal complexes, inorganic solids, crystals, rare earth and rare earth oxide materials, polymers, scintillators, phosphor materials, and materials that exhibit excitonic properties, which may optionally contain one or more dopants;
wherein the nanoparticle has on a surface thereof at least one psoralen compound capable of activation by the emitted UV energy, wherein the at least one psoralen compound is optionally bound to the surface through a linking molecule selected from nuclear transport proteins and cell penetrating peptides.

2. The functionalized nanoparticle of claim 1, wherein the core comprises a rare earth metal oxide.

3. The functionalized nanoparticle of claim 2, wherein the rare earth metal oxide is $Y_2O_3$.

4. The functionalized nanoparticle of claim 2, wherein the rare earth metal oxide is doped with at least one dopant.

5. The functionalized nanoparticle of claim 1, wherein the shell completely covers the core.

6. The functionalized nanoparticle of claim 1, wherein the plasmonics active material is a member selected from the group consisting of gold and silver.

7. The functionalized nanoparticle of claim 1, wherein the psoralen compound is psoralen.

8. The functionalized nanoparticle of claim 1, wherein the psoralen compound is a psoralen derivative.

9. The functionalized nanoparticle of claim 8, wherein the psoralen derivative is 8-MOP.

10. The functionalized nanoparticle of claim 1, wherein the psoralen compound is bound to the shell directly.

11. The functionalized nanoparticle of claim 1, wherein the psoralen compound is bound to the shell through the linking molecule.

12. The functionalized nanoparticle of claim 11, wherein the linking molecule is a nuclear transport protein or cell penetrating peptide selected from the group consisting of TAT, penetratin, MAP, polyarginine, c-Fos, Antp, VP22, and transportan.

13. The functionalized nanoparticle of claim 12, wherein the nuclear transport protein is TAT.

14. A functionalized nanoparticle consisting of:
a core comprising $Y_2O_3$;
a shell comprising gold on at least a portion of the core;
a cell penetrating peptide molecule comprising TAT (48-57) bound to a surface of the shell; and
at least one psoralen compound bound to a plurality of the cell penetrating peptide molecules on a side chain or at a distal terminus of the cell penetrating peptide from the shell.

15. The functionalized nanoparticle of claim 14, wherein the core has an average diameter of 100 nm or less.

16. The functionalized nanoparticle of claim 14, wherein the combination of core and shell has an average diameter of 100 nm or less.

17. The functionalized nanoparticle of claim 16, wherein the average diameter is 30 nm or less.

18. The functionalized nanoparticle of claim 17, wherein the average diameter is 10 nm or less.

19. A method for treatment of a cell proliferation disorder, comprising:
    administering to target cells in a subject in need thereof, the functionalized nanoparticle of claim 1, and
    applying X-ray energy to the target cells, causing activation of the psoralen compound,
    thus causing a change in the target cells treating the cell proliferation disorder.

20. The method of claim 19, wherein the cell proliferation disorder is cancer.

21. The method of claim 20, wherein the target cells are tumor cells.

22. The method of claim 19, wherein the core comprises a material selected from the group consisting of metals, quantum dots, semiconductor materials, scintillation and phosphor materials, materials that exhibit X-ray excited luminescence (XEOL), organic solids, metal complexes, inorganic solids, crystals, rare earth and rare earth oxide materials, polymers, scintillators, phosphor materials, and materials that exhibit excitonic properties.

23. The method of claim 22, wherein the core comprises a rare earth metal oxide.

24. The method of claim 23, wherein the rare earth metal oxide is $Y_2O_3$.

25. The method of claim 23, wherein the rare earth metal oxide is doped with at least one dopant.

26. The method of claim 19, wherein the shell is present on at least a portion thereof.

27. The method of claim 19, wherein the shell coats around an aggregate of nanoparticles.

28. The method of claim 19, wherein the shell comprises a number of isolated nanoislands of metals, metal oxides or metals alloys.

29. The method of claim 26, wherein the shell completely covers the core.

30. The method of claim 26, wherein the plasmonics active material is a member selected from the group consisting of gold and silver.

31. The method of claim 29, wherein the plasmonics active material is a member selected from the group consisting of gold and silver.

32. The method of claim 19, wherein the psoralen compound is psoralen.

33. The method of claim 19, wherein the psoralen compound is a psoralen derivative.

34. The method of claim 33, wherein the psoralen derivative is 8-MOP.

35. The method of claim 19, wherein the psoralen compound is bound to the shell directly.

36. The method of claim 19, wherein the psoralen compound is bound to the shell through a linking molecule.

37. The method of claim 36, wherein the linking molecule is a nuclear transport protein or a cell penetrating peptide.

38. The method of claim 37, wherein the nuclear transport protein or a cell penetrating peptide is a member selected from the group consisting of TAT, penetratin, MAP, polyarginine, c-Fos, Antp, VP22, and transportan.

39. The method of claim 38, wherein the nuclear transport protein is TAT.

40. A method for treatment of a cell proliferation disorder, comprising:
    administering to target cells in a subject in need thereof, the functionalized nanoparticle of claim 14, and
    applying X-ray energy to the target cells, causing activation of the psoralen compound,
    thus causing a change in the target cells treating the cell proliferation disorder.

41. The method of claim 40, wherein the cell proliferation disorder is cancer.

42. The method of claim 41, wherein the target cells are tumor cells.

43. The method of claim 40, wherein the shell is present on at least a portion thereof.

44. The method of claim 40, wherein the shell completely covers the core.

45. The method of claim 40, wherein the psoralen compound is psoralen.

46. The method of claim 40, wherein the psoralen compound is a psoralen derivative.

47. The method of claim 42, wherein the psoralen derivative is 8-MOP.

48. The method of claim 40, wherein the core has an average diameter of 100 nm or less.

49. The method of claim 40, wherein the combination of core and shell has an average diameter of 100 nm or less.

50. The method of claim 49, wherein the average diameter is 30 nm or less.

51. The method of claim 50, wherein the average diameter is 10 nm or less.

52. A pharmaceutical composition, comprising the functionalized nanoparticle of claim 1 and a pharmaceutically acceptable carrier.

53. The pharmaceutical composition of claim 52, wherein the core comprises a rare earth metal oxide.

54. The pharmaceutical composition of claim 53, wherein the rare earth metal oxide is $Y_2O_3$.

55. The pharmaceutical composition of claim 53, wherein the rare earth metal oxide is doped with at least one dopant.

56. The pharmaceutical composition of claim 52, wherein the shell coats around an aggregate of nanoparticles.

57. The pharmaceutical composition of claim 52, wherein the shell comprises a number of isolated nanoislands of metal, metal oxide or metal alloys.

58. The pharmaceutical composition of claim 52, wherein the shell completely covers the core.

59. The pharmaceutical composition of claim 52, wherein the plasmonics active material is a member selected from the group consisting of gold and silver.

60. The pharmaceutical composition of claim 52, wherein the psoralen compound is psoralen.

61. The pharmaceutical composition of claim 52, wherein the psoralen compound is a psoralen derivative.

62. The pharmaceutical composition of claim 61, wherein the psoralen derivative is 8-MOP.

63. The pharmaceutical composition of claim 52, wherein the psoralen compound is bound to the shell directly.

64. The pharmaceutical composition of claim 52, wherein the psoralen compound is bound to the shell through the linking molecule.

65. The pharmaceutical composition of claim 64, wherein the linking molecule is a nuclear transport protein or cell penetrating peptide selected from the group consisting of TAT, penetratin, MAP, polyarginine, c-Fos, Antp, VP22, and transportan.

66. The pharmaceutical composition of claim 65, wherein the nuclear transport protein is TAT.

67. A pharmaceutical composition, comprising the functionalized nanoparticle of claim 14, and a pharmaceutically acceptable carrier.

68. The pharmaceutical composition of claim 67, wherein the core has an average diameter of 100 nm or less.

69. The pharmaceutical composition of claim 67, wherein the combination of core and shell has an average diameter of 100 nm or less.

70. The pharmaceutical composition of claim 69, wherein the average diameter is 30 nm or less.

71. The pharmaceutical composition of claim 70, wherein the average diameter is 10 nm or less.

72. The pharmaceutical composition of claim 67, wherein the psoralen compound is psoralen.

73. The pharmaceutical composition of claim 67, wherein the psoralen compound is a psoralen derivative.

74. The pharmaceutical composition of claim 73, wherein the psoralen derivative is 8-MOP.

* * * * *

UNITED STATES PATENT AND TRADEMARK OFFICE
CERTIFICATE OF CORRECTION

PATENT NO. : 9,662,389 B2
APPLICATION NO. : 12/843188
DATED : May 30, 2017
INVENTOR(S) : Tuan Vo-Dinh et al.

It is certified that error appears in the above-identified patent and that said Letters Patent is hereby corrected as shown below:

In the Specification

Column 4, Line 19, "(1988)]" should read --(1988)].--

Column 9, Line 43, "therein" should read --therein.--

Column 10, Line 43, "nanoparticles" should read --nanoparticles.--

Column 12, Line 20, "2001]" should read --2001].--

Column 16, Line 15, "20030}" should read --20030}.--

Column 16, Line 27, "4701]" should read --4701].--

Column 16, Line 35, "2007]" should read --2007].--

Column 17, Line 3, "nanoparticles" should read --nanoparticles.--

Signed and Sealed this
Ninth Day of October, 2018

Andrei Iancu
*Director of the United States Patent and Trademark Office*